US011591408B2

(12) United States Patent
Gilbert et al.

(10) Patent No.: US 11,591,408 B2
(45) Date of Patent: Feb. 28, 2023

(54) ANTIBODY GLYCOCONJUGATES AND METHODS OF PRODUCTION AND USE

(71) Applicant: National Research Council of Canada, Ottawa (CA)

(72) Inventors: Michel Gilbert, Gatineau (CA); Traian Sulea, Kirkland (CA); Maria L. Jaramillo, Beaconsfield (CA); Yves Durocher, Montreal (CA); Maurizio Acchione, Pierrefonds (CA)

(73) Assignee: National Research Council of Canada, Ottawa (CA)

( * ) Notice: Subject to any disclaimer, the term of this patent is extended or adjusted under 35 U.S.C. 154(b) by 6 days.

(21) Appl. No.: 16/762,672

(22) PCT Filed: Nov. 8, 2018

(86) PCT No.: PCT/CA2018/051410
§ 371 (c)(1),
(2) Date: May 8, 2020

(87) PCT Pub. No.: WO2019/090424
PCT Pub. Date: May 16, 2019

(65) Prior Publication Data
US 2021/0087298 A1 Mar. 25, 2021

Related U.S. Application Data

(60) Provisional application No. 62/583,571, filed on Nov. 9, 2017.

(51) Int. Cl.
| | | |
|---|---|---|
| *C07K 16/28* | (2006.01) | |
| *C07K 16/46* | (2006.01) | |
| *C07K 16/32* | (2006.01) | |

(52) U.S. Cl.
CPC .......... *C07K 16/46* (2013.01); *C07K 16/2863* (2013.01); *C07K 16/32* (2013.01); *C07K 2317/24* (2013.01); *C07K 2317/41* (2013.01); *C07K 2317/55* (2013.01); *C12Y 204/99001* (2013.01)

(58) Field of Classification Search
None
See application file for complete search history.

(56) References Cited

U.S. PATENT DOCUMENTS

| | | | |
|---|---|---|---|
| 6,254,868 B1 | 7/2001 | Leung et al. | |
| 8,133,515 B2 | 3/2012 | Boons et al. | |
| 9,359,439 B2 * | 6/2016 | Goletz | C07K 16/00 |
| 2016/0257764 A1 | 9/2016 | Van Delft et al. | |
| 2017/0362338 A1 * | 12/2017 | Davidson | A61K 47/6851 |

FOREIGN PATENT DOCUMENTS

| | | |
|---|---|---|
| WO | WO2009/067663 A1 | 5/2009 |
| WO | WO2009/067663 A8 | 5/2009 |
| WO | WO2015/157446 A1 | 10/2015 |

OTHER PUBLICATIONS

Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
Ayoub et al., Correct primary structure assessment and extensive glyco-profiling of cetuximab by a combination of intact, middle-up, middle-down and bottom-up ESI and MALDI mass spectrometry techniques, mAbs (2013), 5:5, 699-710. (Year: 2013).*
Arnold et al. (2007) The impact of glycosylation on the biological function and structure of human immunoglobulins. *Annu. Rev. Immunol.* 25:21-50.
Axup et al. (2012) Synthesis of site-specific antibody-drug conjugates using unnatural amino acids. *Proc. Natl. Acad. Sci. USA*. 109:16101-16106.
Beck et al. (2017) Strategies and challenges for the next generation of antibody-drug conjugates. *Nature Reviews Drug Discovery*, vol. 16, pp. 315-337, ISSN 1474-1776.
Ducry et al. (2010) Antibody-drug conjugates: linking cytotoxic payloads to monoclonal antibodies. *Bioconjug. Chem.* 21:5-13.
Gupta et al. (2002) Prediction of glycosylation across the human proteome and the correlation to protein function. *Pac. Symp. Biocomput.* 7:310-22.
Hornak et al. (2006) Comparison of multiple Amber force fields and development of improved protein backbone parameters. *Proteins* 65:712-725.
Huang et al. (1997) The enhanced tumorigenic activity of a mutant epidermal growth factor receptor common in human cancers is mediated by threshold levels of constitutive tyrosine phosphorylation and unattenuated signaling. *J. Biol. Chem.* 272:2927-2935.

(Continued)

*Primary Examiner* — Brad Duffy
*Assistant Examiner* — Cheom-Gil Cheong
(74) *Attorney, Agent, or Firm* — Finnegan, Henderson, Farabow, Garrett & Dunner, LLP.

(57) ABSTRACT

The present invention relates to compounds, compositions, and methods are provided for covalently linking a cargo molecule, such as a therapeutic or a diagnostic agent, to a glycan in the Fab region of an antibody. Also provided are methods of modeling and producing antibodies having de novo Fab glycosylation sites. Also provided are antibody carrier conjugates, methods of using the conjugates.

19 Claims, 16 Drawing Sheets

Specification includes a Sequence Listing.

(56) References Cited

OTHER PUBLICATIONS

Hutchins et al. (2011) Site-specific coupling and sterically controlled formation of multimeric antibody fab fragments with unnatural amino acids. *J. Mol. Biol.* 406:595-603.

International Search Report and Written Opinion of the International Search Authority dated Jan. 23, 2019, received in International Application No. PCT/CA2018/051410.

Jefferis (2005) Glycosylation of recombinant antibody therapeutics. *Biotechnol. Prog.* 21:11-16.

Junutula et al. (2008) Site-specific conjugation of a cytotoxic drug to an antibody improves the therapeutic index. *Nat. Biotechnol.* 26:925-932.

Kirschner et al. (2008) GLYCAM06: a generalizable biomolecular force field. Carbohydrates. *J. Comput. Chem.* 29:622-655.

Lac et al. (2015) Covalent Chemical Ligation Strategy for Mono- and Polyclonal Immunoglobulins at Their Nucleotide Binding Sites. *Bioconjugate Chemistry*, vol. 27, pp. 159-169, ISSN 1043-1802.

Li et al. (2014) Preparation of well-defined antibody-drug conjugates through glycan remodeling and strain-promoted azide-alkyne cycloadditions. *Angew. Chem. Int. Ed. Engl.* 53:7179-7182.

Liu et al. (2017) Comprehensive N-Glycan Profiling of Cetuximab Biosimilar Candidate by NP-HPLC and MALDI-MS. *PLoS ONE* vol. 12, No. 1, pp. e0I70013, ISSN 1932-6203 Retrieved from the Internet: <doi:10.1371/journal.pone.0I70013.

Panowski et al. (2014) Site-specific antibody drug conjugates for cancer therapy. *MAbs.* 6:34-45.

Qian et al. (2007) Structural characterization of N-linked oligosaccharides on monoclonal antibody cetuximab by the combination of orthogonal matrix-assisted laser desorption/ionization hybrid quadrupolequadrupole time-of-flight tandem mass spectrometry and sequential enzymatic digestion. *Anal. Biochem.* 364:8-18.

Raymond et al. (2015) Production of α2,6-sialylated IgG1 in CHO cells. *MAbs.* 7:571-583.

Strop et al. (2013) Location matters: site of conjugation modulates stability and pharmacokinetics of antibody drug conjugates. *Chem. Biol.* 20:161-167.

Van Geel et al. (2015) Chemoenzymatic conjugation of toxic payloads to the globally conserved N-glycan of native mAbs provides homogeneous and highly efficacious antibody-drug conjugates. *Bioconjug. Chem.* 26:2233-2242.

Wakarchuk et al. (2003) Capillary electrophoresis as an assay method for monitoring glycosyltransferase activity. *Methods Mol. Biol.* 213:263-274.

Watson et al. (2015) Preparation of legionaminic acid analogs of sialo-glycoconjugates by means of mammalian sialyltransferases. *Glycoconj. J.* 32:729-734.

Zhou et al. (2014) Site-Specific Antibody-Drug Conjugation through Glycoengineering. *Bioconjug Chem.* vol. 25, pp. 510-520, ISSN 1043-1802.

\* cited by examiner

A
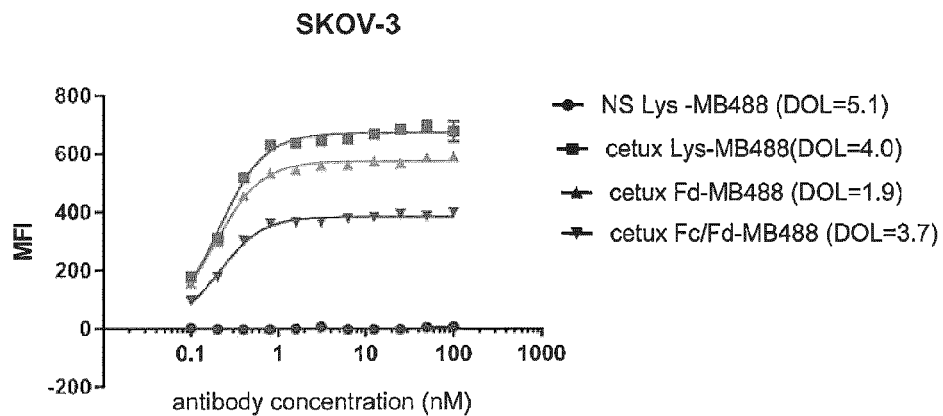
B
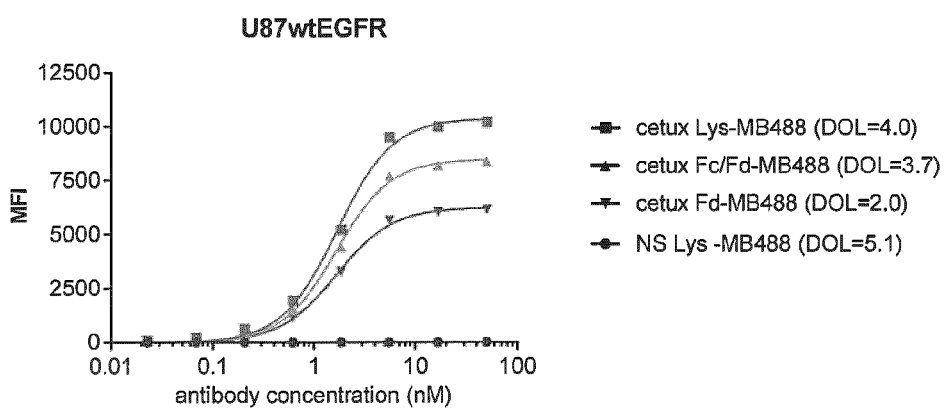
Figure 2

Figure 4

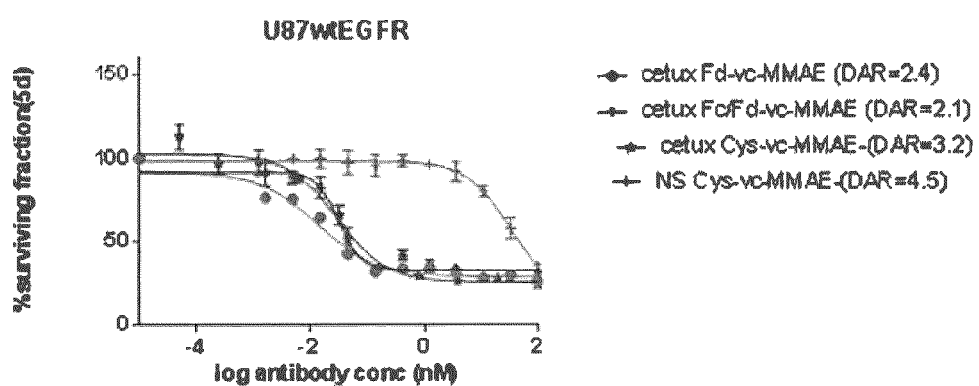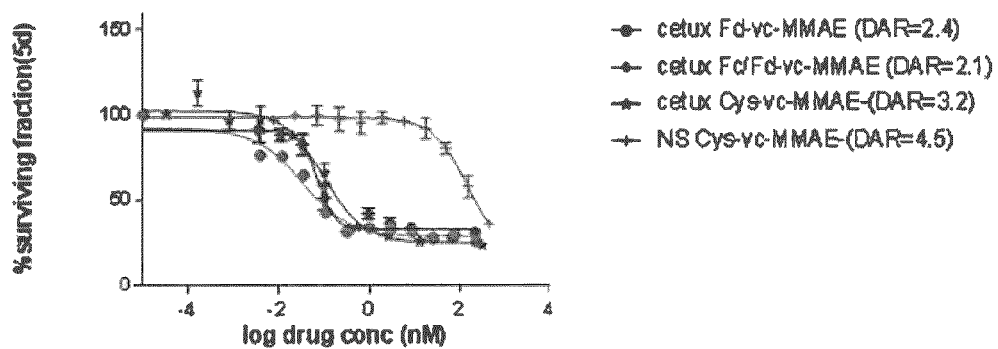
Figure 5

```
hIgG1CH1                    (SEQ ID NO:1)   ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV
hIgG1CH1-K129N              (SEQ ID NO:2)   ASTKGPSVFPLAPSSNSTSGGTAALGCLVKDYFPEPVTVSWNSGALTSGVHTFPAVLQSSGLYSLSSVVTVPSSSLGTQTYICNVNHKPSNTKVDKKV
hIgG1CH1-A158N              (SEQ ID NO:3)   ASTKGPSVFPLAPSSKSTSGGTAALGCLVKDYFPEPVTVSWNSGNLTSGVHTFPAVLQSSGLYSLSSVVTVPSSSLGTQTYICNVNHKPSNTKVDKKV
hIgG1CH1-T191N              (SEQ ID NO:4)   ASTKGPSVFPLAPSSKSTSGGTAALGCLVKDYFPEPVTVSWNSGALTSGVHTFPAVLQSSGLYSLSSVVTVPSSSLGNQTYICNVNHKPSNTKVDKKV
hIgG1CH1-K129N+A158N        (SEQ ID NO:5)   ASTKGPSVFPLAPSSNSTSGGTAALGCLVKDYFPEPVTVSWNSGNLTSGVHTFPAVLQSSGLYSLSSVVTVPSSSLGTQTYICNVNHKPSNTKVDKKV
hIgG1CH1-K129N+T191N        (SEQ ID NO:6)   ASTKGPSVFPLAPSSNSTSGGTAALGCLVKDYFPEPVTVSWNSGALTSGVHTFPAVLQSSGLYSLSSVVTVPSSSLGNQTYICNVNHKPSNTKVDKKV
hIgG1CH1-A158N+T191N        (SEQ ID NO:7)   ASTKGPSVFPLAPSSKSTSGGTAALGCLVKDYFPEPVTVSWNSGNLTSGVHTFPAVLQSSGLYSLSSVVTVPSSSLGNQTYICNVNHKPSNTKVDKKV
hIgG1CH1-K129N+A158N+T191N  (SEQ ID NO:8)   ASTKGPSVFPLAPSSNSTSGGTAALGCLVKDYFPEPVTVSWNSGNLTSGVHTFPAVLQSSGLYSLSSVVTVPSSSLGNQTYICNVNHKPSNTKVDKKV
```

Figure 6A

```
hIgG1CH1    (SEQ ID NO:1)   ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKV
hIgG2CH1    (SEQ ID NO:9)   ASTKGPSVFPLAPSSRSTSGGTAALGCLVKDYFPEPVTVSWNGALTSGVHTFPAVLQSSGLYSLSSVVTVPSSSLGTQTYICNVNHKPSNTKVDKKV
hIgG3CH1    (SEQ ID NO:10)  ASTKGPSVFPLAPSSRSTSGGTAALGCLVKDYFPEPVTVSWNGALTSGVHTFPAVLQSSGLYSLSSVVTVPSSSLGTQTYICNVNHKPSNTKVDKK
hIgG4CH1    (SEQ ID NO:11)  ASTKGPSVFPLAPSSRSTSGGTAALGCLVKDYFPEPVTVSWNGALTSGVHTFPAVLQSSGLYSLSSVVTVPSSSLGIKTYICNVNHKPSNTKVDKKV
```

Figure 6B

ANTIBODY GLYCOCONJUGATES AND METHODS OF PRODUCTION AND USE

RELATED APPLICATIONS

This application is a national phase application under 35 U.S.C. § 371 of international application number PCT/CA2018/051410, filed Nov. 8, 2018, which designated the U.S. and claims the benefit of Priority of U.S. provisional application No. 62/583,571, filed Nov. 9, 2017, each of which is incorporated herein by reference in its entirety.

FIELD OF THE INVENTION

The present invention relates to modified antibodies. In particular, the present invention relates to modified antibodies comprising at least one N-linked glycan having a functionalized sialic acid in the Fab region. Such antibodies may be used in the production of antibody conjugates.

BACKGROUND

Antibody conjugates are useful for delivering a cargo, including but not limited to therapeutic and/or diagnostic agents, to specific targets.

Manufacture of antibody conjugates using conventional chemistry approaches nonselectively links cargo to antibodies by electrophilic modification of lysine or cysteine residues using N-hydroxysuccinimide ester or maleimide-activated drugs, respectively (Ducry et al., *Bioconjug. Chem.* 2010, 21: 5-13). These conjugation methods yield heterogeneous mixtures of products that differ in the sites and stoichiometry of modification. Nonspecific incorporation of the cargo on the antibody can result in a conjugate that has reduced targeting as compared to antibody alone if the incorporation happens in a region of the antibody involved with binding of the epitope or reduced Fc effector function if the incorporation is in a region involved with the Fc effector function. In addition, production of a heterogenous product may lead to difficulties obtaining an optimal cargo to antibody ratio. Finally, the resulting heterogeneous mixture can significantly impact the pharmacokinetic properties of ADCs and efficacy in vivo (Panowski et al., *MAbs* 2014, 6: 1-12). Therefore there is a pressing demand for the development of site-specific conjugation methodologies.

The selectivity of site specific incorporation of the cargo on the antibody allows for the production of a more homogeneous product and may avoid potential interference with binding to the antibody target epitope, or reduced Fc effector function, due to conjugations at or near the CDRs or Fc region, which can happen with less specific conjugation protocols. Site-specific conjugates may also be selected to improve the biophysical properties (like aggregation propensity), physicochemical properties that impact on stability and phamacokinetic properties, such as half-life in the circulation. Furthermore, site specific incorporation may be used to refine cargo to antibody ratio and/or to generate higher stoichiometry cargo containing antibodies when site-specific conjugations at different sites are combined. Homogeneous ADCs have been obtained by genetic engineering of antibodies to incorporate additional cysteines, (Junutula et al., *Nat. Biotechnol.* 2008, 26: 925-932.), unnatural amino acids (a) Hutchins et al, *Mol. Biol.* 2011, 406: 595-603. b) Axup et al., *PNAS USA.* 2012, 109: 16101-16106) or tags for transamination reactions (Strop et al., *Chem. Biol.* 2013, 20:161-167).

Non-genetic methods for generating antibody conjugates (i.e. that rely on the native mAb sequence) have been developed by modifying naturally occurring glycan residues for the purpose of attaching payloads. In one approach, consecutive enzymatic glycan trimming of antibodies at Asn 297 to core GlcNAc residues and subsequent chemoenzymatic addition of azido-modified sugar introduces an attachment point for copper-free click conjugation with a payload (van Geel et al., *Bioconjug. Chem.* 2015, 26: 2233-2234; US Patent Application 2016/0257764). However, this method suffers from an inability to conjugate more than one payload per N-linker glycan (i.e. with a maximum drug to antibody ratio (DAR) of 2. Li et al. incorporated a functionalized sialic acid by contacting the antibody containing at least one N-linked glycan with functionalized CMP-Neu5Ac9N$_3$ and the sialytransferase ST6 beta-galactoside alpha-2,6-sialyltransferase 1 (ST6Gal1) which targets both Fc and Fab glycans and covalently attaching a cargo to the functionalized sialic acid (Li et al., *Angew. Chem. Int. Ed. Engl.* 2014, 53: 7179-7182, WO2015/157446). However, in all the above-mentioned cases, the enzymes used for enzymatic remodeling of glycans will modify the naturally occurring glycan residues found at Asn-297 which may impact Fc dependent effector functions in this region.

SUMMARY OF THE INVENTION

An object of the present invention is to provide antibody glycoconjugates and methods of production and use. In accordance with an aspect of the present invention, there is provided an antibody comprising at least one N-linked glycan having functionalized sialic acid in the Fab region, optionally in the Fd region, optionally wherein said functionalized sialic acid is added by a bacterial sialyltransferase, optionally derived from *Actinobacillus suis*. In certain embodiments the one or more engineered glycosylation sites are in the framework regions of the Fd, optionally at amino acid positions 129, 158 and/or 191. In certain embodiments, the functionalized sialic acid is an azido-modified sialic acid, optionally a functionalized N-acetylneuraminic acid, optionally N-azidoacetylneuraminic acid.

In accordance with another aspect of the invention, there is provided an antibody which has been engineered to contain one or more glycosylation sites in the Fab region, optionally in the Fd region. In certain embodiments, the one or more engineered glycosylation sites are in the framework regions of the Fd. In certain embodiments, the one or more engineered glycosylation sites are located at amino acid position 129, 158 and/or 191. In certain embodiments, each of said one or more engineered glycosylation sites comprises a N-linked glycan having a functionalized sialic acid, optionally wherein said functionalized sialic acid is an azido-modified sialic acid, optionally N-azidoacetylneuraminic acid.

The antibody may be any type of antibody including but not limited to an IgG, IgG1, IgA2, IgE or IgM antibody.

In accordance with another aspect of the invention, there is provided a conjugate comprising (i) the antibody of the invention and (ii) a cargo covalently attached to each of said functionalized sialic acid, optionally wherein the cargo comprises a detectable agent or a therapeutic agent.

In accordance with another aspect of the invention, there is provided a modified cetuximab comprising at least one N-linked glycan having a functionalized sialic acid in the Fab region, preferably in the Fd region, optionally comprising a cargo covalently attached to said functionalized sialic acid. In certain embodiments, the functionalized sialic acid is added by a bacterial sialyltransferase, optionally derived from *Actinobacillus suis*.

In accordance with another aspect of the invention, there is provided a modified trastuzumab engineered to comprise at least one N-linked glycan having a functionalized sialic acid in the Fab region, optionally in the Fd region, optionally the trastuzumab is genetically modified to comprise mutations in the Fd region selected from the group of K129N; A158N; T191N; K129N+A158N+T191N; A158N+T191N; K129N+T191N and K129N+A158N. In certain embodiments, the at least one of said N-linked glycan comprises a functionalized sialic acid, optionally wherein said functionalized sialic acid is an azido-modified sialic acid, optionally N-azidoacetylneuraminic acid. In certain embodiments, the modified trastuzumab further comprises a cargo covalently attached to said functionalized sialic acid. In certain embodiments, the functionalized sialic acid is added by a bacterial sialyltransferase, optionally derived from *Actinobacillus suis*.

In another aspect of the invention, there is provided a method of modifying an antibody, the method comprising contacting an antibody comprising at least one N-linked glycan in the Fab region of said antibody with a bacterial sialyltransferase specific for N-linked glycan in the Fab region and a functionalized CMP-sialic acid for a time and under conditions sufficient to covalently attach a functionalized sialic acid to said N-linked glycan, wherein optionally said functionalized sialic acid is an azido-modified sialic acid, optionally functionalized N-acetylneuraminic acid (ex. N-azidoacetylneuraminic acid). In certain embodiments, the bacterial sialyltransferase is derived from *Actinobacillus suis*. In certain embodiments, the method further comprises covalently linking a cargo to the functionalized sialic acid of the antibody to yield an antibody conjugate, optionally wherein said step of covalently linking a cargo is carried out using click chemistry. In certain embodiments of the method, the antibody is cetuximab. In certain embodiments of the method, the antibody is trastuzumab genetically modified to comprise at least one Fab glycolysation site, optionally, wherein said trastuzumab is genetically modified to comprise mutations in Fd region selected from the group of K129N; A158N; T191N; K129N+A158N+T191N; A158N+T191N; K129N+T191N; K129N+A158N.

In another aspect of the present invention, there is provided a modified antibody modified by the method of the invention.

In another aspect of the present invention, there is provided a method of detecting a cell expressing an antigen, said method comprising contacting said cell with the conjugate of the invention and detecting binding of said antibody conjugate, wherein said antibody specifically binds said antigen.

In another aspect of the present invention, there is provided a method of targeting a therapeutic agent to a cell expressing an antigen, said method comprising contacting said cell with the conjugate of the invention, wherein said antibody specifically binds said antigen.

In another aspect of the present invention, there is provided a method of producing a conjugate, the method comprising (i) specifically modifying at least one N-linked glycan in the Fab region of said antibody with a functionalized sialic acid, optionally wherein said specifically modifying at least one N-linked glycan in the Fab region of said antibody with a functionalized sialic acid comprises contacting said antibody comprising at least one N-linked glycan in the Fab region of said antibody with a sialyltransferase derived from an *Actinobacillus* sp. bacterium and said functionalized CMP-sialic acid for a time and under conditions sufficient to covalently attach said functionalized sialic acid to said N-linked glycan; (ii) covalently linking a cargo to the functionalized sialic acid on the at least one N-linked glycan in the Fab region; (iii) modifying at least one further N-linked glycan in said antibody with functionalized sialic acid, wherein said modifying at least one further N-linked glycan in said antibody with a functionalized sialic acid comprises contacting said antibody comprising at least one N-linked glycan in said antibody with ST6 beta-galactoside alpha-2,6-sialyltransferase 1 and said functionalized CMP-sialic acid for a time and under conditions sufficient to covalently attach said functionalized sialic acid to said N-linked glycan; and (iv) covalently linking a second cargo to the functionalized sialic acid on the at least one further N-linked glycan.

Abbreviations and Acronyms

AST-03: alpha-2,3-sialyltransferase from *Actinobacillus suis* expressed as a maltose-binding fusion in *Escherichi coli*.
Cetux: cetuximab
DBCO: dibenzocyclooctyne
DBCO-PEG4-vc-PAB-MMAE: Clickable MMAE drug with self-immolative linker (Val-Cit-PAB).
DAR: Drug to antibody ratio
DOL: Degree of labeling
MC-vc-PAB-MMAE: MMAE drug with maleimide and self-immolative linker (Val-Cit-PAB)
MMAE: monomethyl Auristatin E
Neu5NAz: N-azidoacetylneuraminic acid
NS: Non specific antibody (Synagis)
Trast: trastuzumab
ST6Gal1: sialtransferase ST6 beta-galactoside alpha-2,6-sialyltransferase 1
TCEP: tris(2-carboxyethyl)phosphine
wt: wild type Abbreviations of Conjugates with MB488 Fluorescent Label NS Lys-MB488: Non specific antibody conjugated through Lys
cetux Lys-MB488: Cetuximab conjugated through Lys
cetux Fc/Fd-MB488: Cetuximab conjugated through Neu5NAz on Fc and Fd glycans
cetux Fd-MB488: Cetuximab conjugated through Neu5NAz on Fd glycans
trast Lys-MB488: trastuzumab wt conjugated through Lys
trast Fc-MB488: trastuzumab wt conjugated through Neu5NAz on Fc glycans
trast L189N-MB488 trastuzumab L189N mutant conjugated through Neu5NAz on Fd glycans
trast A158N-MB488: trastuzumab A158N mutant conjugated through Neu5NAz on Fd glycans
trast K129N-MB488: trastuzumab A158N mutant conjugated through Neu5NAz on Fd glycans Abbreviations of MMAE Conjugates with Controlled Release (vc-PAB) Linkers NS Cys-vc-MMAE: Non specific antibody conjugated through Cys
cetux Cys-vc-MMAE: Cetuximab conjugated through Cys cetux Fd-vc-MMAE: Cetuximab conjugated through Neu5NAz on Fd glycans cetux Fc/Fd-vc-MMAE: Cetuximab conjugated through Neu5NAz on Fc and Fd glycans trast Lys-vc-MMAE: trastuzumab wt conjugated through Lys trast Fc-vc-MMAE: trastuzumab wt conjugated through Neu5NAz on Fc glycans trast L189N-vc-MMAE: trastuzumab L189N mutant conjugated through Neu5NAz on Fd glycans trast A158N-vc-MMAE: trastuzumab A158N mutant conjugated through Neu5NAz on Fd glycans trast T191N-vc-MMAE: trastuzumab A158N mutant conjugated through Neu5NAz on Fd glycans Residue Numbering Sequential residue numbering of the CH1 domain from the IgG heavy chain is used herein, starting with residue A114 in SEQ ID NOS: 1-11. The correspondence between this numbering and other widely accepted numbering schemes is given below for the CH1 mutations mentioned throughout this disclosure:

| Sequential numbering | IMGT numbering CH1 | EU numbering | Kabat numbering |
|---|---|---|---|
| 129 | 16 | 133 | 129 |
| 158 | 45 | 162 | 165 |
| 189 | 76 | 193 | 198 |
| 191 | 78 | 195 | 200 |

BRIEF DESCRIPTION OF THE FIGURES

FIG. 2 demonstrates binding of glyco-engineered cetuximab labeled with MB488 to EGFR expressing cells.

FIG. 4 illustrates mass spectrometry analysis of cetux Fc/Fd-vc-MMAE (deconvoluted spectra).

FIG. 5 demonstrates growth inhibitory effect of glyco-engineered cetuximab conjugated with DBCO-vc-PAB-MMAE in U87 glioblastoma cancer cells engineered to overexpress EGFR. Potency was determined according to concentration of antibody (Panel A) or MMAE (Panel B).

FIG. 6 illustrates the sequence alignment (6A) between the wild-type CH1 domain of the human IgG1 (SEQ ID NO:1), its single-point mutants introducing glycosylation sites at three positions, i.e., K129N, A158N and T191N (SEQ ID NO:2-4), and double (SEQ ID NO:5-7) and triple (SEQ ID NO:8) combinations thereof. Selected sites for de novo glycosylation appear to be well-conserved among the CH1 domains of other human IgG isoforms (SEQ ID NO: 9-11) according to a sequence alignment (6B).

DETAILED DESCRIPTION

Figure 1:
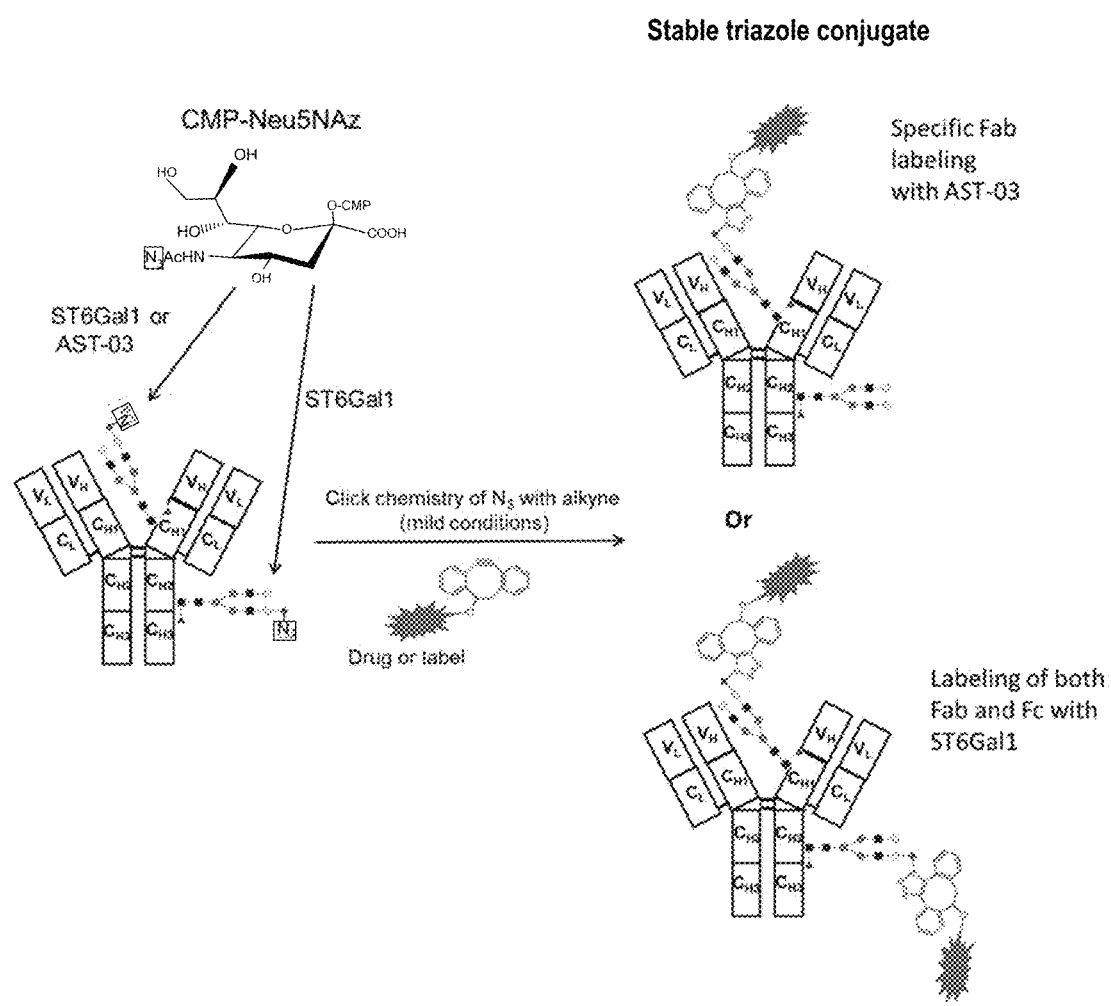
FIG. 1 provides an overview of the conjugation to antibody glycans using azido sialic acid. Neu5NAz is transferred to the Fc and Fab glycans using ST6Gal1 or specifically to the Fab glycan using AST-03. A label or a drug can then be covalently attached to the functionalized sialic acid.

The present invention provides antibody cargo conjugates, modified antibodies useful for the production of such conjugates, methods for the production of the modified antibodies and methods for the production of the antibody cargo conjugates. Also provided are methods of producing antibodies comprising de novo glycosylation sites and antibodies comprising de novo glycosylation sites.

The present invention is based on the discovery that some bacterial sialyltransferases catalyze sialylation of N-linked glycans in the Fab region of antibodies but do not catalyze sialylation of N-linked glycans in the Fc region of antibodies. By exploiting these bacterial sialyltransferases, antibodies comprising at least one N-linked glycan in the Fab region may be modified to include a functionalized sialic acid in a site specific manner while, in certain embodiments, preserving antigen binding and/or Fc dependent effector functions. In specific embodiments, the antigen binding affinity and/or Fc dependent effector function of the modified antibody is comparable to unmodified antibody. The functional group on the sialic acid provides a specific site for covalently attaching a cargo. Accordingly, the present invention provides antibodies comprising at least one N-linked glycan having a functionalized sialic acid in the Fab region.

In certain embodiments, at least one N-linked glycan having functionalized sialic acid is in the Fd region of the antibody. In specific embodiments, at least one N-linked glycan is in the CH1 domain of the Fd region. In certain embodiments, the modified antibody further comprises at least one N-linked glycan having functionalized sialic acid in the Fc region. In certain embodiments, the modified antibody does not comprise any N-linked glycans having a functionalized sialic acid in the Fc region.

The modified antibody may comprise at least one, at least two, at least three N-linked glycans having functionalized sialic acid in the Fab region of an antibody.

Antibodies which May be Modified

The antibodies which may be modified to include at least one N-linked glycan having functionalized sialic acid in the Fab region may include any antibody having at least one N-linked glycan in the Fab region. For example, the antibody may be of any class, such as an IgM, IgA, IgD, IgE, or IgG class, or antibody subclass (such as IgG1 or IgA2) or a fragment thereof so long as the antibody or fragment thereof has at least one N-linked glycan in the Fab region. In certain embodiments, the antibody is an IgG1 antibody. The antibody may be derived from a human, a mouse, a rat, another mammal, a chimeric or genetically engineered antibody. In certain embodiments, the antibody is a humanized antibody. In specific embodiments, the antibody is a humanized mouse antibody. The antibodies may be a monoclonal or polyclonal antibody. The antibody may be produced by a hybridoma or a cell line which expresses the antibody.

Non-limiting examples of antibodies that may be modified include cetuximab, trastuzumab, rituximab, brentuximab, inotuzumab, gemtuzumab, lorvotuzumab, glembatumumab, milatuzumab, labestuzumab, alemtuzumab, bevacizumab, panitumumab, ibritumomab, or tositumomab. Antibodies having no native N-linked glycosylation sites in the Fab region may be genetically engineered to include at least one N-linked glycosylation site in the Fab region. Such antibodies include but are not limited to trastuzumab.

In certain embodiments, the modified antibody is a modified cetuximab comprising at least one N-linked glycan having a functionalized sialic acid in the Fab region. In specific embodiments, the at least one N-linked glycan having a functionalized sialic acid is in the Fd region of the antibody.

In certain embodiments, the modified antibody is a modified trastuzumab antibody which has been engineered to contain one or more glycosylation sites in the Fab region. In specific embodiments, the modified trastuzumab comprises at least one N-linked glycan having a functionalized sialic acid in the Fab region. In further specific embodiments, the trastuzumab is genetically modified to comprise mutations in the Fd region selected from the group of K129N; A158N; T191N; K129N+A158N+T191N; A158+T191N; K129N+T191N and K129N+A158N.

Antibodies suitable for modification may be generated by any suitable methods known in the art. Methods include but are not limited to the use of hybridoma cells, recombinant expression systems, and phage display technologies, immunization methods or a combination thereof. Methods of antibody purification are also known in the art and include but are not limited to chromatography, centrifugation and differential solubility.

Commercial antibodies may also be modified to produce the modified antibodies and conjugates of the present invention.

In certain embodiments, the N-linked glycosylation site(s) in the Fab region is naturally occurring and as such, the number and location of N-linked glycans having a functionalized sialic acid will be limited to the number and location of the naturally occurring N-linked glycosylation sites. Alternatively, the antibody has been genetically engineered to contain at least one N-linked glycosylation site(s) in the Fab region. In certain embodiments, the antibodies include both naturally occurring and genetically engineered N-linked glycosylation sites in the Fab region.

Modifications

The present invention provides a modified antibody comprising at least one N-linked glycan having a functionalized sialic acid in the Fab region. Due to the biantennary structure of the glycans, each branch may contain one functionalized sialic acid residue, thus permitting up to 2 payload molecules to be conjugated per N-linked glycan. This is a property which can be useful for generating higher order payloads (DAR>2).

As used herein, sialic acid includes N- or O-substituted derivatives of neuraminic acid, 2-keto-5-acetamido-3,5-dideoxy-D-glycero-D-galactononulosonic acid (Neu5Ac), and 2-keto-3-deoxy-D-glycero-D-galactononic acid (KDN). For example, sialic acid and its derivatives can include and are sometimes referred to as N-acetylneuraminic acid, NANA, NeuAc, Neu5Ac, or Neu5Gc. Functionalized sialic acid as the term is used herein refers to a sialic acid having a functional group that can participate in a covalent linkage with a functionalized cargo molecule. The sialic acid functional group serves as the site for the covalent linkage of the cargo molecule to the antibody.

In one embodiment, the functional group is positioned at C-9 of the sialic acid. In another embodiment, the functional group is positioned at C-5 of the sialic acid. Functionalized sialic acid can contain one, two or more functional groups capable of covalent linkage with a cargo molecule, positioned at C-9, C-5 or any other suitable position on the sialic acid, such as, without limitation, C-1, C-2, C-4, C-7, or C-8. A functionalized sialic acid containing more than one functional group may contain the same or different functional groups.

Exemplary functional groups include but are not limited to azide, nitrone, nitrile oxide, azoxy, diazo, acyl diazo, and trans-cyclooctene. In certain embodiments, the modified antibody comprising at least one N-linked glycan has an azido-modified sialic acid in the Fab region. In specific embodiments, the functionalized sialic acid is N-azido-acetylneuraminic acid (Neu5NAz).

In certain embodiments the functional group or groups present on the functionalized sialic acid allow for the covalent attachment of a cargo molecule via click chemistry. Appropriate click chemistry methods are known in the art and non-limiting examples are described in U.S. Pat. No. 8,133,515 and WO/2009/067663.

Conjugates

The present invention further provides a conjugate comprising the modified antibody with at least one N-linked glycan having a functionalized sialic acid in the Fab region and a cargo molecule covalently attached at each of the functionalized sialic acids in the antibody. For illustrative purposes and as a non-limiting example, antibodies comprising two N-linked glycans having a functionalized sialic acid may have two to four cargo molecules attached while antibodies comprising four N-linked glycans having functionalized sialic acid may have four to eight cargo molecules attached. Such conjugates may further comprise cargo molecules attached to other sites in the antibody including for example, N-linked glycans in the Fc region. In one embodiment, all the cargo molecules attached to the antibody are the same. In another embodiment, different types of cargo molecules are attached to the antibody. In a specific embodiment, a first type of cargo molecule is attached to the at least one N-linked glycan having a functionalized sialic acid in the Fab region and a second type of cargo molecule is attached to N-linked glycans in the Fc region of the antibody.

Non-limiting examples of cargo include a cytotoxic drug, a cytostatic agent, a toxin, a radioisotope or radionuclide, a nucleotide, an RNA, a DNA, an antibiotic, an immunosuppressive agent, a fluorophore, a dye, a protein, or any combination thereof.

In certain embodiments, the cargo comprises a detectable agent. In specific embodiments, the detectable agent is selected from a radioisotope, a paramagnetic label such as gadolinium or iron oxide, a fluorophore, a fluorescent agent, Near Infra-Red (NIR) fluorochrome or dye such as Cy5.5, an echogenic microbubble, an affinity label such as biotin, avidin, etc, a detectable protein-based molecule, nucleotide, quantum dot, nanoparticle, nanowire, nanotube and any other suitable agent that may be detected by imaging methods.

In certain embodiments, the cargo comprises a therapeutic agent. In specific embodiments, the therapeutic agent is a cytotoxic or chemotherapeutic agent. Non-limiting examples of cytotoxic or chemotherapeutic agent include microtubule inhibiting agents (such as maytansines and auristatins), DNA damaging agents (such as calicheamicin and duocarmycin), RNA polymerase inhibitors (such as alpha-amanitin), anti-metabolites, agents that react with DNA (such as alkylating agents, coordination compounds, platinum complexes, DNA cross-linking compounds), inhibitors of transcription enzymes, tyrosine kinase inhibitors, topoisomerase inhibitors, DNA minor-groove binding compounds, antimitotic agents (such as vinca alkyloids and taxanes), antitumor antibiotics, hormones, and enzymes.

In certain embodiments, the conjugate comprises multiple types of cargo, including for example multiple types of diagnostic agents, multiple types of therapeutic agents, a diagnostic agent and a therapeutic agent.

In certain embodiments, the cargo molecule includes or is modified to include a functional group that reacts with the modified antibody. For example, if conjugation utilizes a click reaction, the cargo includes the partner reactive moiety that allows it to participate in the click reaction with the modified antibody. In one embodiment, the cargo molecule includes or can be modified to include a functional group that reacts with an azido group on the functionalized sialic acid of the modified antibody.

Optionally, the cargo molecule can include a linker region. In one embodiment, the linker region may be non-cleavable. In another embodiment, the linker region may be degradable or enzyme cleavable or reduced in the reducing environment of the cell. In one embodiment, the linker region can include an acid-labile region which becomes unstable and degrades at low pH, including, for example, the pH of a lysosome.

Methods of Modifying Ab

The present invention further provides methods of modifying an antibody, the method comprising specifically modifying at least one N-linked glycan in the Fab region of said antibody with a functionalized sialic acid. In one embodiment, the antibody comprising the at least one N-linked glycan in the Fab region is contacted by at least one sialyltransferase specific for N-linked glycan in the Fab region and a functionalized sialic acid substrate, for a time and under conditions sufficient to covalently attach the functionalized sialic acid to the at least one N-linked glycan. In certain embodiments, prior to sialylation, the antibody is treated with sialidase to remove Fab sialic acid.

The functionalized sialic acid substrate is typically a nucleotide associated sialic acid, such as a CMP-sialic acid. In certain embodiments, the functionalized CMP-sialic acid is a CMP-azido-modified sialic acid. In specific embodiments, the functionalized sialic acid substrate can be CMP-Neu5Ac9N$_3$ or alternatively CMP-Neu5NAz. The functionalized CMP-sialic acid may be produced by contacting cytidine triphosphate (CTP) and CMP-sialic acid synthetase for a time and under conditions sufficient to produce a functionalized CMP-sialic acid.

The sialyltransferase, ST6Gal1, has been previously found to catalyze the sialylation of N-linked glycans in both the Fc and Fab regions of antibodies using functionalized CMP-sialic acid derivative as a substrate. Surprisingly, it was found that certain bacterial sialyltransferases catalyze sialylation of N-linked glycans in the Fab region of antibodies but not N-linked glycans in the Fc region of antibodies. Accordingly, these sialyltransferases may be used to specifically modify N-linked glycans in the Fab region of antibody with a functionalized sialic acid.

The bacterial sialyltransferase includes sialyltransferase derived from Gram negative bacterium such as bacterium from the Pasteurellaceae family and *Photobacterium* spp. from the family Vibrionaceae.

In certain embodiments, the bacterial sialyltransferase is derived from an *Actinobacillus* sp., including but not limited to *Actinobacillus suis* bacterium (GenBank Accession #AFU19871). In certain other embodiments, the bacterial sialyltransferase is derived from CAZy glycosyltransferase family 80.

In certain embodiments, the bacterial sialyltransferase comprises an amino acid sequence having at least 60%, at least 70%, at least 80%, at least 90%, or 100% identity to the amino acid sequence as set forth in GenBank Accession #AFU19871 or an active fragment thereof.

In certain embodiments, the bacterial sialyltransferase comprises an amino acid sequence comprises an amino acid sequence having at least 60%, at least 70%, at least 80%, at least 90%, or 100% identity to the amino acid sequence as set forth below (SEQ ID NO:12) or an active fragment thereof:

```
                                        (SEQ ID NO: 12)
MERTPQLQAVDIYIDFATIPSLSYFLHFLKHKHDDQRLRLFSLARFEMPQ

TLIEQYEGIIQFSRNVEHNVEPLLEQLQTILSQEGKQFELHLHLNLFHSF

EMPLNLSPTYTQYKEKISKIVLHLYDDGSEGVMKQYQLQKSSSLVQDLAA

TKASLVSLFENGEGSFSQIDLIRYVWNAVLETHYYLLSDHFLLDEKLQPL

KAELGHYQLLNLSAYQYLSSEDLLWLKQILKIDTELESLMQKLTAQPVYF

FSGTIFFNISFEDKQRLANIHAILIREHLDPNSQLFIGEPYLFVFKGHPN

SPEINQALREYYPNVIFLPENIPFEILTLLGFSPQKIGGFASTIHVNSEQ

SKLAKLFFLTSTDEQERQLSDGYIKQYALAQAMLEMQLVSQEQVYYCSLS

S
```

In specific embodiments, there is provided a method of producing an antibody conjugate comprising one type of cargo covalently attached to glycans in the Fab region and a second type of cargo covalently attached to glycans in the Fc region. The method comprises conjugating the cargo to the Fab region by specifically modifying at least one N-linked glycan in the Fab region of the antibody with a functionalized sialic acid by contacting the antibody with a sialyltransferase comprising the sequence as set forth in GenBank Accession #AFU19871 and a functionalized CMP-sialic acid for a time and under conditions sufficient to covalently attach the functionalized sialic acid to a N-linked glycan. Next, the cargo is covalently linked to the functionalized sialic acid to produce an antibody conjugate comprising a cargo covalently attached to glycans in the Fc region. This conjugate is further modified by contacting it with ST6Gal11 and functionalized CMP-sialic acid for a time and under conditions sufficient to covalently attach the functionalized sialic acid to the at least one N-linked glycan in the Fc region. A second cargo is then covalently attached to the functionalized sialic acid on the at least one N-linked glycan in the Fc region to produce antibody conjugate comprising one type of cargo covalently attached to glycans in the Fab region and a second type of cargo covalently attached to glycans in the Fc region.

Methods of Engineering Antibodies to Insert De Novo Glycosylation Sites

There is diversity in the number and location of naturally occurring N-linked glycosylation sites. For example, only 20% of human IgG1 antibodies have naturally occurring Fab glycoslation sites (Jefferis, *Biotechnol. Prog.* 2005, 21: 11-16). IgA2, IgE and IgM have naturally occurring Fab glycoslation sites (Arnold et al., *Annu. Rev. Immunol.* 2007, 25: 21-50). The glycosylation profiles/glycosylation sites of antibodies can be readily determined using techniques known in the art. In addition, for many publicly available antibodies, the glycosylation profiles/glycosylation sites are known in the art. In specific examples, cetuximab has a site within framework 3 of the variable portion of the heavy chain (Qian et al., Anal Biochem. 2007, 364(1):8-18) and as such has two Fd N-glycosylation sites while trastuzumab has no naturally occurring Fd N-glycosylation sites.

Accordingly, the present invention provides methods for engineering at least one de novo N-linked glycosylation site(s) in the Fab region. Also provided are polynucleotides encoding the engineered antibody and cells expressing the engineered antibodies. In certain embodiments, the antibodies have only genetically engineered N-linked glycosylation sites in the Fab region. In certain embodiments, the antibodies include both naturally occurring and genetically engineered N-linked glycosylation sites in the Fab region. Introduction of novel N-linked sequons is known in the art. See, for example, U.S. Pat. No. 6,254,868.

In certain embodiments, there is provided a method of modifying an antibody to insert one or more de novo glycosylation sites in the Fab region of said antibody, said method comprising genetically engineering a polynucleotide encoding the light chain of said antibody and/or a polynucleotide encoding the heavy chain to insert one or more mutations which create one or more de novo glycosylation sites in the Fab region of said antibody. Glycosylation sites are known in the art and include, for example, NX(T/S), where X can be any amino acid except proline and aspartate. Accordingly, in specific embodiments, the antibody sequence is modified to insert one or more NX(T/S) sequons. In further specific embodiments, the one or more NX(T/S) sequons are introduced with a single mutation. The use of a single mutation to introduce the site may minimize perturbation of the 3D structure of the antibody. Methods of site directed mutagenesis to introduce specific mutations in a sequence are known in the art and include for example PCR-based methods.

In certain embodiments, there is provided a method of producing an antibody glycosylated in the Fab region of said antibody, said method comprising co-expressing, in a cell that allows glycosylation, polynucleotides encoding the light chain and the heavy chain of said antibody, wherein said polynucleotide encoding the light chain and/or said polynucleotide encoding the heavy chain has been genetically engineered to insert one or more mutations which create one or more de novo glycosylation sites in the Fab region of said antibody, and isolating said antibody or antibody fragment.

In certain embodiments, there is provided a method of optimizing drug/antibody ratio of an antibody conjugate comprising a cargo linked via N-linked glycans on the antibody, the method comprising introducing one or more de novo glycoslylation sites in the Fab region of the antibody.

Molecular Modeling

The present invention also provides general in silico methods of molecular modeling to design the modified antibodies with novel glycosylation sites and conjugates, which are exemplified by the modified antibodies and conjugates of the present invention. In silico molecular modeling may be used to determine antibody 3D structure and the impact of the change of amino acid sequence and/or glycosylation status on the 3D structure. Homology with proteins having a known 3D structure may be used to model 3-D structures of proteins, including the structure antibodies. The crystal structure of many proteins is known in the art and is readily available. For example, a typical crystallographic structure of a Fab may be obtained from the Protein Data Bank (PDB). In silico molecular modeling programs are known in the art. For example, structure examination of the crystal structure may be performed using PyMol (The PyMOL Molecular Graphics System, Version 1.8 Schrodinger, LLC). Structure examination may include, for example, residue/side-chain surface exposure calculation, secondary structure, polar contacts, hydrophobic neighboring residues, and distance measurements. Structural manipulation of the crystal structure, including, for example, site residue mutagenesis, N-GlcNAc linkage and conformational analysis, may be performed using Sybyl (Tripos, Inc., St. Louis, Mo.). Structural refinement may be performed using the Amber and Glycam force fields (Hornak et al., *Proteins,* 2006, 65: 712-725; Kirschner et al., *J Comput Chem.,* 2008, 29: 622-655). N-glycosylation scores may be computed via the online server NetNGlyc 1.0 DTU Health Tech; Gupta and Brunak, Pacific Symposium on Biocomputing, 2002, 7: 310-322).

Accordingly, in certain embodiments, molecular modeling is used to determine appropriate sites for introduction of novel N-linked glycosylation sites. In specific embodiments, the structural template for molecular design is based on a typical crystallographic structure of a Fab at high resolution.

A number of factors may be considered when selecting de novo sites which include but are not limited to including sites that minimally impact the 3D structure for example by selecting mutations and glycosylation sites that are exposed and not engaged in the folding of the Fd, choosing sites that maintain epitope binding and biophysical properties (including for example solubility, stability and lower aggregation) and choosing sites that do not impact effector functions, selecting sites that do not interfere with other glycosylation sites (either naturally occurring or engineered). In addition, for antibody drug conjugates (ADCs), a drug to antibody ratio (DAR) of 2-4 is generally recognized as optimal to obtain sufficient potency while preserving good physicochemical properties for the ADCs.

In a specific embodiment, the selection criteria for de novo glycosylation sites is as follows:
(1) NX(T/S) sequon is introduced by a single mutation;
(2) Single mutation adds N residue not T/S residue in order to limit modifications to a single position (if T/S is mutated then both N and T/S positions are modified);
(3) Mutation to N residue does not replace hydrophobic residues L, I, V, M, and F;
(4) Mutation to N residue does not replace conformationally special residues P and G;
(5) Side chain of wild-type residue to be mutated is surface exposed;
(6) Side chain of wild-type residues to be mutated is not engaged in significant hydrophobic contacts or hydrogen bonds with other atoms of the mAb;
(7) Side chain of wild-type residue to be mutated is not part of α-helix or β-strand secondary structure elements;
(8) Introduced N residue side chain can adopt a conformation that projects the side chain nitrogen atom towards the solvent;
(9) N-linked monosaccharide GlcNAc can adopt a conformation that does not clash with atoms of the mAb and is projected towards the solvent;
(10) N-linked monosaccharide GlcNAc is at least 15 Å away from the nearest atom in the variable domain;
(11) De novo glycosylation sites are at least 15 Å away from each other (defined as the distance between Cα atoms of the residues mutated to N residues).

Methods of Producing the Conjugate

The present invention further provides methods of producing the modified antibody cargo conjugates of the present invention. The cargo may be covalently attached to modified antibody by methods known in the art including enzymatically, chemically, or chemoenzymatically. In one embodiment of the invention, the cargo is conjugated to the antibody via click reactions. For example, the cargo may be conjugated to the antibody via Staudinger ligation using modified phosphines or copper(I)-catalyzed cycloaddition with terminal alkynes (CuAAC). In certain embodiments, the cargo is conjugated to the antibody via azido/alkyne click chemistry to produce a triazole conjugate.

Compositions and Methods of Use

The present invention further provides compositions comprising and methods of using the modified antibodies and conjugates. Antibody conjugates may be used to target cargo to a particular extracellular or cell surface antigen, including but not limited to a tissue specific antigens, tumor antigens, cell surface antigens, disease or injury specific antigens, pathogen antigens including viral, parasitic or bacterial antigens. Depending on the nature of the cargo, such conjugates may be used in the detection of an antigen, the diagnosis and/or treatment of a variety of diseases and/or conditions.

In certain embodiments there is provided a method of detecting a cell expressing an antigen, the method comprising contacting said cell with the conjugate of invention and detecting binding of said antibody conjugate, wherein said antibody specifically binds the antigen.

In certain embodiments there is provided a method of targeting a therapeutic agent to a cell expressing an antigen, said method comprising contacting said cell with the conjugate of the invention, wherein the antibody specifically binds said antigen.

In certain embodiments, the disease is cancer. Exemplary cancers include but are not limited to a carcinoma of the bladder, breast, cervix, colon, endometrium, kidney, lung, esophagus, ovary, prostate, pancreas, skin (i.e. melanoma), stomach, and/or testes.

In certain embodiments, the disease is an infectious disease. In specific embodiments, the infectious disease is a viral infectious disease including HIV, HBV and HCV.

The conjugates may or may not be endocytosed by cells to which the conjugates are bound. A worker skilled in the art would readily appreciate that depending on the nature of the cargo, the cargo may be active when conjugated or alternatively may need to be released from the conjugate. Accordingly, in certain embodiments, the conjugate binds a cell expressing the target antigen and is not endocytosed. In other embodiments, the conjugate binds a cell expressing the target antigen, the conjugate is internalized and processed within endosomes and/or lysomes and the cargo is released from the conjugate.

The conjugates may be administered alone or in combination with other agents, including other agents including diagnostic agents, biologically active agents or therapeutic agents.

The conjugate may be in the form of a pharmaceutical composition for administration that is formulated to be appropriate for the selected mode of administration, and pharmaceutically acceptable diluent or excipients, such as buffers, surfactants, preservatives, solubilizing agents, isotonicity agents, stabilizing agents, carriers, and the like. Various delivery systems are known and may be used to administer the conjugates. Non-limiting examples include encapsulation in liposomes, microparticles and microcapsules.

The conjugates may be formulated as a pharmaceutical composition for administration and may include, and pharmaceutically acceptable diluent or excipients, such as buffers, surfactants, preservatives, solubilizing agents, isotonicity agents, stabilizing agents, carriers, and the like.

The conjugates may be administered by a variety of methods known in the art including but not limited to enteral, parenteral, intradermal, intramuscular, intraperitoneal, intravenous, subcutaneous, intranasal, epidural, intraventricular, intrathecal and oral routes. Administration may be systemic or local.

EXAMPLES

Example 1

Specific Conjugation to the Fd Glycan of Cetuximab Using Bacterial Sialyltransferases Removal of Sialic Acid from Cetuximab Sialic acid was removed by treating 9.6 mg of cetuximab (final concentration 1 mg/mL) with 0.96 unit of a recombinant sialidase from *Micromonospora viridifaciens* (construct MNV-02) for 2 h at 37° C. in 50 mM Hepes pH 6.5. Removal of the sialic acid was confirmed by isoelectrofocusing using a PhastSystem (GE Healthcare Life Sciences), PhastGel IEF 3-9 and staining with Coomassie blue. The MNV-02 sialidase includes a 6-His tag and was removed by binding to 0.6 mL of Nickel Sepharose excel resin (GE Healthcare Life Sciences) while cetuximab was recovered in the flowthrough. An assay for sialidase activity measured residual activity which required removal by binding of the cetuximab to a HiTrap Protein A column (GE Healthcare Life Sciences) as described below.

Addition of Galactose

Galactose was added using a recombinant version of the human beta-1,4-galactosyltransferase 1 expressed in *E. coli*. The reaction mix included approximately 9 mg of de-sialylated cetuximab, 500 mU of beta-1,4-galactosyltransferase 1, 10 mM $MnCl_2$, 10 mM UDP-Gal, 50 mM Hepes pH 6.5 and 100 mM NaCl. The reaction was performed at 37° C. for 24 h. The cetuximab was purified by applying half of the reaction mix to a 1 mL Protein A column equilibrated with PBS buffer pH 7.5 (2 separate runs total were performed). The cetuximab was eluted with 100 mM citrate buffer pH 3 and the buffer was replaced with PBS pH 7.5 by desalting on a 5 mL HiTrap desalting column (GE Healthcare Life Sciences). The material was concentrated to 2.94 mg/mL (total of 7.64 mg recovered) using an Amicon Ultra-4 centrifugal filter unit with a 10,000 NMWL.

Production and Purification of AST-03

A synthetic gene corresponding to the sequence of open reading frame ASU2_08685 (GenBank Accession #AFU19871) from *Streptococcus suis* was ordered from Eurofins MWG Operon and delivered as an insert in plasmid pEX-K4. The insert was amplified using the Phusion® High-Fidelity DNA polymerase (New England Biolabs Inc.) and the primers AS-01 (5' CGTAGCGATACATATG-GAAAGAACCCCCCAACTAC 3', 35 mer, Ndel site in italics, SEQ ID NO:13) and AS-02 (5' CTGAAGGTCGA-CATTATGAGGACAAACTACAATAATAC 3', 38 mer, Sall site in italics; SEQ ID NO:14). The PCR product was digested with Ndel and Sall and cloned in pCWori+(−lacZ) containing the sequence encoding the *E. coli* maltose-binding protein (without the leader peptide) and the thrombin cleavage site, giving construct AST-03. *E. coli* AD202 containing construct AST-03 was grown in 2 YT medium containing 150 µg/mL ampicillin and 2 g/L glucose. The culture was incubated at 37° C. until $A_{600}$=0.5, induced with 1 mM IPTG, and then incubated overnight at 25° C. The cells were broken using an Avestin C5 Emulsiflex cell disruptor (Avestin, Ottawa) and the AST-03 sialyltransferase was purified by affinity chromatography on amylose resin following the manufacturer's instructions (New England Biolabs, Beverly, Mass.). The activity of the purified AST-03 sialyltransferase was measured using 0.5 mM 6-(5-fluorescein-carboxamido)-hexanoic acid succimidyl ester (FCHASE)-labeled LacNAc, 0.5 mM CMP-Neu5Ac, 10 mM $MnCl_2$ and 50 mM Hepes pH 7 in a 5 min assay at 37° C. The samples were analyzed by capillary electrophoresis (CE) as described previously (Wakarchuk and Cunningham, *Methods Mol Biol*. 2003, 213: 263-274). Quantitation of the reactions was performed by integration of the CE trace peaks using the MDQ 32 Karat software (Beckman, Calif.). One unit of activity was defined as the amount of enzyme that produces one µmol of Neu5Ac-LacNAc-FCHASE in one minute.

Synthesis of CMP-Neu5NAz

N-azidoacetyl-D-mannosamine (ManNAz) was obtained from Sussex Research Laboratories. The synthesis of N-azidoacetylneuraminic acid (Neu5NAz) was performed using a recombinant form of the Pm1715 sialic acid aldolase from *Pasteurella multocida*. The reaction mix with the Pm1715 sialic acid aldolase included 20 mM ManNAz, 100 mM sodium pyruvate and 100 mM Tris pH 8.6 and was incubated at 37° C. for 18 h. The CMP-Neu5NAz was obtained by adding a recombinant form of the CMP-NeuAc synthetase from *Campylobacter jejuni* as well as 13 mM CTP and 63 mM $MgCl_2$. The reaction was performed at 37° C. for 1.5 h and the enzymes were removed by running the reaction mix on an Amicon Ultra-15 centrifugal filter unit with a 10,000 NMWL. The filtrate was diluted 30-fold with water and applied to a 5 mL HiTrapQ HP column (7 runs total). The column was developed with a gradient of 0 to 0.25 M $NH_4HCO_3$ and the fractions containing CMP-Neu5NAz were identified by capillary electrophoresis analysis using a P/ACE MDQ system (Beckman Coulter, Fullerton, Calif., USA) equipped with a diode array detector (electropherogram acquired at 271 nm). Capillaries were bare silica 50 µm×60.2 cm with a detector at 50 cm, the running buffer was 25 mM sodium tetraborate, pH 9.4 and separations were performed at 27 kV for 30 min. Fractions containing CMP-Neu5NAz were lyophilized with sodium chloride as counterion (3 NaCl for one CMP-Neu5NAz).

Production and Purification of ST6Gal1

ST6Gal1 was produced and purified as previously described (Watson et al., *Glycoconj. J.* 2015 32: 729-734). In summary, the codon-optimized (human codon bias) gene encoding the human ST6Gal1 protein (GenBank accession #P15907) intralumenal domain (aa 27-406) with a human VEGFa (GenBank accession #P15692) signal peptide linked at its N-terminus and a C-terminal GHHHHHHHHHHG tag (SEQ ID NO: 15) at its C-terminus was chemically synthesized by GenScript (Piscataway, N.J.) and cloned into the pTT5 mammalian expression vector. The secreted ST6Gal1 enzyme was expressed in CHO-EBNA1 (CHO-3E7) cells and the clarified culture medium supernatant was harvested at 8 days post-transfection and the secreted ST6Gal1 was purified by immobilized metal-affinity chromatography (IMAC).

Addition of Neu5NAz to the Fd Glycans of Cetuximab

Neu5NAz was added to the Fd glycans of cetuximab using the AST-03 alpha-2,3-sialyltransferase. The reaction mix included 1 mg/mL de-sialylated and galactosylated cetuximab (total of 1.69 mg), 50 mM Hepes pH 7, 10 mM $MnCl_2$, 1 mM CMP-Neu5NAz and 55 mU of AST-03. The reaction was performed at 37° C. for 21 h. The cetuximab (Fd-Neu5NAz) was purified by applying the reaction mix to a 1 mL Protein A column equilibrated with PBS buffer pH 7.5. The cetuximab(Fd-Neu5NAz) was eluted with 100 mM citrate buffer pH 3 and the buffer was replaced with PBS pH 7.5 by desalting on a 5 mL HiTrap desalting column (GE Healthcare Life Sciences). The material was concentrated to 2.64 mg/mL (total of 1.22 mg recovered) using an Amicon Ultra-4 centrifugal filter unit with a 10,000 NMWL.

Addition of Neu5NAz to the Fc and Fd Glycans of Betuximab

Neu5NAz was added to the Fc and Fd glycans of cetuximab using ST6Gal1. The reaction mix included 1 mg/mL de-sialylated and galactosylated cetuximab (total of 3.1 mg), 50 mM Hepes pH 7.5, 10 mM $MnCl_2$, 1 mM CMP-Neu5NAz and 78 mU of ST6Gal1. The reaction was performed at 37° C. for 24 h. The cetuximab (Fc/Fd-Neu5NAz) was purified by applying the reaction mix to a 1 mL Protein A column equilibrated with PBS buffer pH 7.5. The cetuximab (Fc/Fd-Neu5NAz) was eluted with 100 mM citrate buffer pH 3 and the buffer was replaced with PBS pH 7.5 by desalting on a 5 mL HiTrap desalting column (GE Healthcare Life Sciences). The material was concentrated to 2.84 mg/mL (total of 2.27 mg recovered) using an Amicon Ultra-4 centrifugal filter unit with a 10,000 NMWL.

Labeling of Glyco-Engineered Cetuximab with MB488-DBCO

The glyco-engineered cetuximab (Fd-Neu5NAz) and cetuximab (Fc/Fd-Neu5NAz), both at 1.45 mg/mL (0.6 mg total), were reacted with 0.2 mM MB488-DBCO (Click Chemistry Tools) in PBS pH 7.4 for 24 h at 25° C. in the dark. The unreacted MB488-DBCO was removed by loading the reactions on PD Miditrap G-25 columns (GE Healthcare Life Sciences) and eluting with PBS pH 7.5. The degree of labeling was calculated using a molar extinction coefficient of 75,000 $M^{-1}$ $cm^{-1}$ at 494 nm for MB488 and a correction factor of 0.26 at 280 nm. A molar extinction coefficient of 217,376 $M^{-1}$ $cm^{-1}$ at 280 nm for cetuximab was used. Pooling the most concentrated fractions yielded 0.31 mg of cetux Fd-MB488 with a degree of labeling (DOL) of 1.94 while the recovery for cetux Fc/Fd-MB488 was 0.38 mg with a degree of labeling of 3.83.

For comparison purposes, randomly labeled version of antibodies were generated by conjugated NHS ester (or succinimidyl ester) of Alexa Fluor® 488 to the primary amines (R—NH2) using conventional kits (ThermoFisher cat no 20000).

Click Reactions of Glyco-Engineered Cetuximab with DBCO-PEG4-VC-PAB-MMAE

The glyco-engineered cetuximab (Fd-Neu5NAz) at 1.86 mg/mL (0.65 mg total), was reacted with 0.13 mM DBCO-PEG4-VC-PAB-MMAE (Levena Biopharma) in 10% dimethylacetamide, 100 mM potassium phosphate, 20 mM NaCl, 2 mM EDTA, pH 7.2 for 24 h at 23° C. in the dark. The glyco-engineered cetuximab (Fc/Fd-Neu5NAz) was reacted under the same conditions except that the concentration was 2 mg/mL (0.7 mg total) and the DBCO-PEG4-VC-PAB-MMAE concentration was 0.14 mM. The unreacted DBCO-PEG4-VC-PAB-MMAE was removed by loading the reaction on a 2 mL Zeba Spin Desalting column (Pierce) and eluting with 20 mM succinate, 0.02% Tween 20, pH 5.5, 6% trehalose. The desalting step was repeated for a total of three times. The drug to antibody ratio was calculated using molar extinction coefficients of 33,095 $M^{-1}$ $cm^{-1}$ at 248 nm and 7,615 $M^{-1}$ $cm^{-1}$ at 280 nm for clicked DBCO-PEG4-VC-PAB-MMAE. We used molar extinction coefficients 73,117 $M^{-1}$ $cm^{-1}$ at 248 nm of 210,863 $M^{-1}$ $cm^{-1}$ at 280 nm for cetuximab. The recovery was 0.47 mg of cetux Fd-vc-MMAE with a DAR of 2.4 while the recovery for cetux Fc/Fd-vc-MMAE was 0.57 mg with a degree of labeling of 2.1.

For comparison purposes, vc-MMAE was randomly conjugated to reduced inter chain cysteine (Cys) residues using the following methodology: prior to conjugation, an absorbance scan of the protein (antibody) sample (2 µL) is measured on a Nanodrop 2000 instrument. The ratio of the absorbance at 248/280 nm is determined and used to calculate the extinction coefficient of the antibody to be conjugated at 248 nm. This value will be used to determine the drug:antibody ratio (DAR) for the conjugate produced. Lyophilized MC-vc-PAB-MMAE is solubilized in dimethylacetamide to a final concentration of 10 mM. This stock is aliquoted and stored at −20° C. until used. Prior to conjugation, each protein sample must have its surface-accessible disulphide bonds reduced to generate reactive free thiols. The level of DAR is controlled by adjusting the degree of reduction of disulphide bonds by increasing the concentration of reducing agent. To achieve the desired specified DAR, a three point scouting experiment using three different concentrations of TCEP (24, 40 and 55 µM) with a final concentration of antibody of 10 µM. The reduction is initiated by addition of TCEP from a 25× working stock into the antibody solution in the following buffer: 100 mM sodium phosphate, 20 mM NaCl, 2 mM EDTA, pH 7.2. The mixture is incubated at 37° C. for 3 h. A 10-fold molar excess (100 µM) of MC-vc-PAB-MMAE is added to the reaction mixture from a 20× working stock in DMA. The final concentration of co-solvent in the reaction is 5% v/v. The reaction is incubated at 25° C. for 1 h. During this incubation, 3×0.5 mL 7K MWCO Zeba Spin columns are pre-equilibrated in standard formulation buffer (20 mM Succinate, 0.02% w/v Polysorbate-20, pH 6.0). After the reaction is complete, Polysorbate-20 is added to a final concentration of 0.02% w/v prior to passing the reaction mixture consecutively through the pre-equilibrated Zeba columns. To the eluant, $\frac{1}{5}^{th}$ volume of 36% Trehalose solution (in formulations buffer) is added. Absorbance measurements of the conjugate at 248 nm and 280 nm are used to calculate the DAR, and the sample measured for monomeric purity by HPLC-Superdex size-exclusion chromatography. The DAR for each of the three TCEP concentrations is plotted vs the DAR determined and the slope of the linear relationship used to determine the optimal concentration to reach the desired DAR. The above procedure is then repeated using these optimal conditions at the specified scale. Final concentration reported for the conjugate is adjusted to compensate for contribution at 280 nm from attached drug.

Glycoprofile Analysis by LC-MS of Glyco-Engineered Cetuximab and of Conjugates

Glycoprofile analysis by LC-MS was performed as described in Raymond et al. (*Mabs* 2015, 7: 571-583). Fc/2 ($C_H2$-$C_H3$) and Fd ($V_H$—$C_H1$) glycopeptides were obtained by digestion of the antibodies (20 µg, 2 mg/mL) with 20 U of "FabRICATOR" IdeS (Genovis) in 50 mM Tris-HCl pH 8 at 37° C. for 30 min, followed by reduction with 20 mM DTT (Sigma) at 56° C. for 30 min. The resulting digests were analyzed by LC-MS using an Agilent HP1100 Capillary LC system (Agilent Technologies) coupled to a LTQ-Orbitrap XL mass spectrometer (Thermo Fisher Scientific) equipped with a high flow electrospray ionization source. Five µg of digested antibody was loaded on a Poros R2 column (2.1×30 mm) (Applied Biosystems) heated to 80° C. Mobile phases were 0.1% formic acid in water (A) and 100% acetonitrile (B) preheated to ~80° C. A linear gradient of 10%-75% B over 12 min (3 mL/min) was used to resolve the Fc/2 and Fab antibody fragments. The HPLC eluent was split to 100 µL/min just before the electrospray source of the LTQ-Orbitrap XL and MS spectra was acquired from m/z 400 to 2000 at a resolution of 15,000. LC-MS spectra were viewed in Xcalibur® (Thermo Fisher Scientific). Molecular weight profiles were generated with the MassLynx© Max- Ent1 deconvolution software (Waters). Databridge (Waters) was used to convert the protein LC-MS spectra into a format that was compatible with MaxEnt1. The abundances of the glycans were calculated on the basis of signal heights observed in the molecular weight profiles. The percentage of a given glycan was obtained as the signal height of the Fc/2 or Fd glycopeptide carrying this glycan divided by the total signal heights of the glycans identified in the profile.

Cell Culture

Binding and functional testing was performed on cultured cell that are known to express the EGFR. SKOV3 (human ovarian adenocarcinoma) cell lines were obtained from ATCC and cultured according to supplier's recommendations. U87wtEGFR glioblastoma cell lines were engineered to overexpress EGFR (Huang et al., *J. Biol. Chem.* 1997, 272: 2927-2935) (provided by Web Cavanee). Cells were passaged twice a week and used within 4-6 weeks for all cell lines.

Target Binding by Flow Cytometry

Fluorescently labeled antibodies were tested for binding to SKOV3 and U87wtEGFR. Adherent cells were dissociated with non-enzymatic Sigma Cell Dissociation Solution (Cat. No. C5789). Cells suspensions were added to polypropylene, V-bottom 96-well plates and incubated for 2 h on ice with 488-labeled antibodies at concentrations ranging from 100 nM to 0.001 nM. After incubation and washes, cell viability was determined using Fixable viability dye 450 (20 min on ice). Stained cells were fixed in 1% Formaldehyde at 4° C. and stored at 4° C. until acquisition which was performed next day.

Data acquisition was performed in the LSR-Fortessa Flow cytometer (Beckton Dickinson) equipped with FACS Diva Software and HTS unit (automated sampling in 96-well plates). FACS data was exported into Excel data files and MFI (Median Fluorescence intensity) of the AF488-stained, alive (single cells) peak was taken for calculations. Background subtraction was calculated for all wells using the MFI values of the cells incubated in the absence of secondary antibody.

Background subtracted data was analyzed in GraphPad 6.0 using the One-site specific binding with Hill slope non-linear regression curve fit model to determine apparent Bmax and Kd for each of the test articles.

Growth Inhibition Assay

Drug-conjugated antibodies were tested for their effects on viability on glioblastoma cell lines that were engineered to overexpress EGFR (U87wtEGFR). Cells were seeded at 500 cells/well in 384-well plates (Corning® 384 Well White Flat Bottom Polystyrene TC-Treated Microplates, Cat. #3570). Cells were allowed to grow for five days in the presence of serial dilutions of the test articles or benchmark controls ranging from 100 nM to 0.0017 nM. After five days (37° C., 5% $CO_2$, humidified incubator), the number of viable cells in culture was determined using CellTiterGlo (Promega, Madison), based on quantitation of the ATP present in each well, which signals the presence of metabolically active cells.

Signal output was measured on a luminescence plate reader (Envision, Perkin Elmer) set at an integration time of 0.1 sec. Integration time is adjusted to minimize signal saturation at high ATP concentration Data analysis: Each concentration point (S) is normalized to the negative control wells (NC) and expressed as % survival. Dose-response curves of % survival vs. log concentration were fit using GraphPad Prism 6.0 with a four parameter logistic model to estimate $IC_{50}$ and maximum efficacy.

Results

Cell surface binding of fluorescent-conjugated anti-EGFR antibodies was determined on EGFR expressing cell lines (FIG. 2) as described above. As a negative control, binding due to an irrelevant fluorescently labeled antibody (NS antibody, Lys) was included to determine levels of non-targeted binding.

All conjugated cetuximab antibodies were shown to bind SKOV3 and EGFR overexpressing U87 glioblastoma cells relative to the non-targeted antibody. Furthermore, anti-EGFR antibodies that were conjugated to their glycan residues (cetux Fd-MB488 and cetux Fc/Fd-MB488) were similar in binding affinity to when compared to antibodies labeled on random lysine residues (Lys) (see Table 1 and FIG. 2).

TABLE 1

Apparent Kd determinations of MB488-labeled mAbs in SKOV3 and U87wtEGFR cells. Results are expressed as: average +/− stdev (n)

| | Apparent Kd (nM) | |
|---|---|---|
| | SKOV3 | U87wtEGFR |
| NS Lys-MB488 | No binding | No binding |
| cetux Lys-MB488 | 0.19 +/− 0.01 (2) | 1.69 |
| cetux Fd-MB488 | 0.17 +/− 0.03 (2) | 1.66 |
| cetux Fc/Fd-MB488 | 0.19 +/− 0.02 (2) | 1.66 |

Glycoprofile Analysis by LC-MS of Glyco-Engineered Cetuximab and of Conjugates

Mass spectrometry analysis was used to determine the glycoprofile of cetuximab labeled on Fd glycans with Neu5NAz using AST-03 (FIG. 3) and of cetuximab labeled with Neu5NAz on Fc/Fd using ST6Gal1 (FIG. 4), and following conjugation with DBCO-PEG4-vc-PAB-MMAE. The quantification of species is detailed in Tables 2 and 3 below.

TABLE 2

Figure 3:
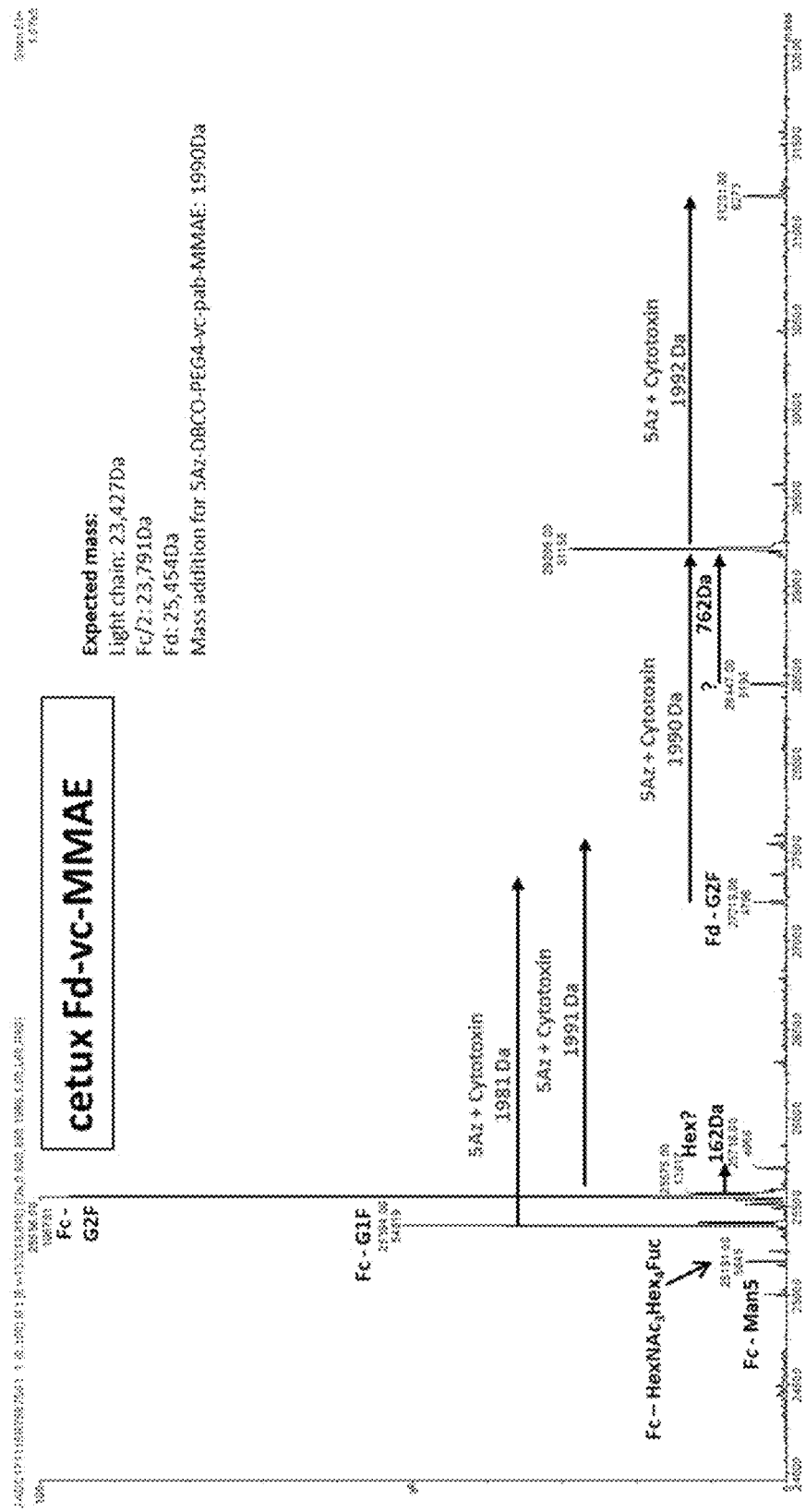
FIG. 3 illustrates mass spectrometry analysis of cetux Fd-vc-MMAE (deconvoluted spectra).

Glycoprofile of cetux Fd-vc-MMAE (see FIG. 3)

| Glycan | % MS signal intensity |
|---|---|
| Fc glycosylation site (Fc/2 fragment) | |
| HexNAc2Hex5 (Man5) | 1 |
| HexNAc3Hex4Fuc | 3 |
| HexNAc4Hex3 (G0) | 0 |
| HexNAc4Hex3Fuc (G0F) | 0 |
| HexNAc4Hex4 (G1) | 1 |
| HexNAc4Hex4Fuc (G1F) | 26 |
| HexNAc4Hex5 (G2) | 6 |
| HexNAc4Hex6 (G2 + Hex) | 7 |
| HexNAc4Hex5Fuc (G2F) | 51 |

TABLE 2-continued

Glycoprofile of cetux Fd-vc-MMAE (see FIG. 3)

| Glycan | % MS signal intensity |
|---|---|
| HexNAc4Hex6Fuc (G2F + Hex) | 2 |
| HexNAc4Hex4Fuc (G1F) + NeuAc5N3 + Cytotoxin | 1 |
| HexNAc4Hex5Fuc (G2F) + NeuAc5N3 + Cytotoxin | 1 |
| Fab glycosylation site (Fd fragment) | |
| HexNAc4Hex5Fuc (G2F) | 11 |
| HexNAc4Hex5Fuc (G2F) + NeuAc5N3 + Cytotoxin | 74 |
| HexNAc4Hex5Fuc (G2F) + 2(NeuAc5N3 + Cytotoxin) | 15 |

TABLE 3

Figure 4:
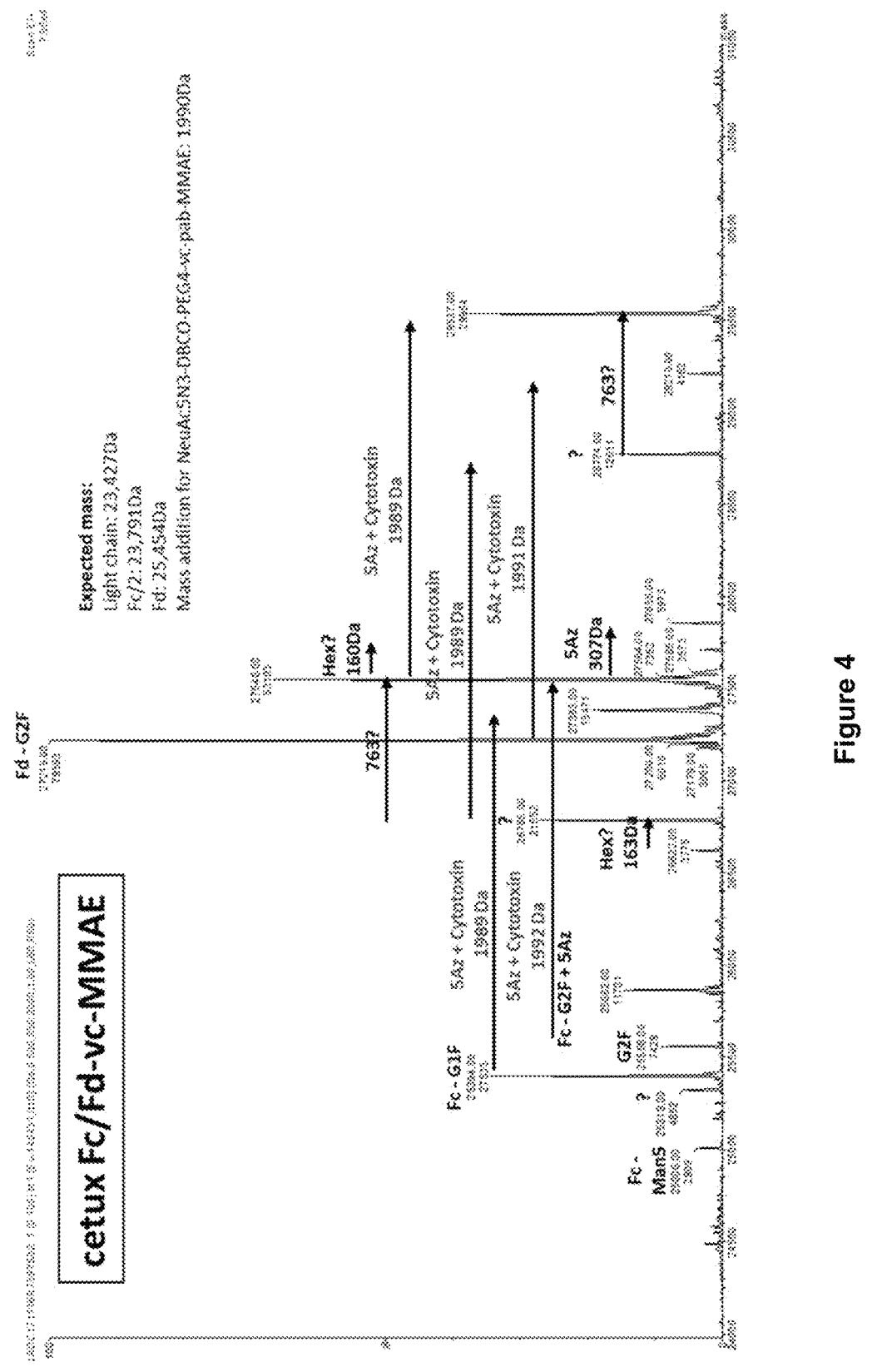

Glycoprofile of cetux Fc/Fd-vc-MMAE (see FIG. 4)

| Glycan | % MS signal intensity |
|---|---|
| Fc glycosylation site (Fc/2 fragment) | |
| HexNAc2Hex5 (Man5) | 2 |
| HexNAc2Hex6 (Man6) | 1 |
| HexNAc3Hex4Fuc | 0 |
| HexNAc4Hex3 (G0) | 0 |
| HexNAc4Hex3Fuc (G0F) | 0 |
| HexNAc4Hex4 (G1) | 1 |
| HexNAc4Hex4Fuc (G1F) | 17 |
| HexNAc4Hex5 (G2) | 1 |
| HexNAc4Hex5Fuc (G2F) | 5 |
| HexNAc4Hex4Fuc (G1F) + NeuAc5N3 | 1 |
| HexNAc4Hex5Fuc (G2F) + NeuAc5N3 | 7 |
| HexNAc4Hex4Fuc (G1F) + NeuAc5N3 + Cytotoxin | 9 |
| HexNAc4Hex5Fuc (G2F) + NeuAc5N3 + Cytotoxin | 32 |
| HexNAc4Hex5Fuc (G2F) + 2(NeuAc5N3 + Cytotoxin) | 18 |
| HexNAc4Hex5Fuc (G2F) + NeuAc5N3 + Cytotoxin + Hex | 2 |
| HexNAc4Hex5Fuc (G2F) + NeuAc5N3 + Cytotoxin + NeuAc5N3 | 4 |
| Fab glycosylation site (Fd fragment) | |
| HexNAc4Hex5Fuc (G2F) | 95 |
| HexNAc4Hex5Fuc (G2F) + NeuAc5N3 + Cytotoxin | 5 |

The glycoprofile of cetux Fd-vc-MMAE shows that 89% of the Fab glycoforms are modified with at least one drug while there is only 2% of the Fc glycoforms that are modified with MMAE. The glycoprofile of cetux Fc/Fd-vc-MMAE showed the opposite specificity (more drug on the Fc glycoforms than on the Fd glycoforms). However, other experiments have determined that ST6Gal1 can also modify efficiently the Fd glycoforms (data not shown).

Effects of MMAE-conjugated anti-EGFR ADCs on the viability of EGFR overexpressing U87 glioblastoma cells was determined as described above. As a negative control, cell viability due to an irrelevant antibody drug conjugate (NS antibody, Lys) was tested to determine levels of non-targeted growth inhibition.

All conjugated cetuximab antibodies were shown to be active in causing growth inhibition in EGFR overexpressing U87 glioblastoma cells relative to the non targetted ADC. In particular, anti-EGFR antibodies that were conjugated to their glycan residues (cetux Fd-vc-MMAE, and cetux Fc/Fd-vc-MMAE) were more or as potent in their ability to cause growth inhibition as compared to antibodies labeled on random Cys residues (Cys) (FIG. 5A). This was shown to be the case when ADC potency was calculated based on the concentration of the ADC or drug added (MMAE $IC_{50}$, FIG. 5B). See FIG. 5 and Table 4 below.

TABLE 4

Potency determinations of MMAE-glyco-engineered cetuximab in EGFR overexpressing U87 glioblastoma cells.

| ADC | ADC $IC_{50}$ (nM) | MMAE $IC_{50}$ (nM) |
|---|---|---|
| NS Cys-vc-MMAE | 34 | 155 |
| cetux Cys-vc-MMAE | 0.03 | 0.095 |
| cetux Fd-vc-MMAE | 0.014 | 0.03 |
| cetux Fc/Fd-vc-MMAE | 0.032 | 0.07 |

Example 2

Specific Conjugation to De Novo N-Glycosylation Sites in the CH1 Domain of Fd of Trastuzumab

Design of De Novo Glycosylation Sites in the CH1 Domain of Fd

There are advantages to specifically introduce glycosylation sites in the CH1 domain of mAbs. The main aspects of the structure-based design of de novo glycosylation sites within CH1 focus on providing significant surface exposure of the glycosylation sequon and as well as minimal change in stability upon introduction of the sequon and the attached carbohydrate moiety.

Selection Criteria of De Novo Glycosylation Sites (1) NX(T/S) sequon is introduced by a single mutation;
(2) Single mutation always adds N residue not T/S residue in order to limit modifications to a single position (if T/S mutated then both N and T/S positions are modified);
(3) Mutation to N residue does not replace hydrophobic residues L, I, V, M, and F;
(4) Mutation to N residue does not replace conformationally special residues P and G;
(5) Side chain of wild-type residue to be mutated is surface exposed;
(6) Side chain of wild-type residues to be mutated is not engaged in significant hydrophobic contacts or hydrogen bonds with other atoms of the mAb;
(7) Side chain of wild-type residue to be mutated is not part of α-helix or β-strand secondary structure elements;
(8) Introduced N residue side chain can adopt a conformation that projects the side chain nitrogen atom towards the solvent;
(9) N-linked monosaccharide GlcNAc can adopt a conformation that does not clash with atoms of the mAb and is projected towards the solvent;
(10) N-linked monosaccharide GlcNAc is at least 15 Å away from the nearest atom in the variable domain;
(11) De novo glycosylation sites are at least 15 Å away from each other (defined as the distance between Cα atoms of the residues mutated to N residues).

The structural template for molecular design was based on a typical crystallographic structure of a Fab at high resolution. The crystal structure with PDB code 3MXW solved at 1.8-Å resolution was retrieved from the PDB RCSB Protein Data Bank; PMID: 20504762). Structure examination was done using PyMol (The PyMOL Molecular Graphics System, Version 1.8 Schrödinger, LLC), including residue/side-chain surface exposure calculation, secondary structure, polar contacts, hydrophobic neighboring residues, and distance measurements. Structural manipulation was done in Sybyl (Tripos, Inc., St. Louis, Mo.), including site residue mutagenesis, N-GlcNAc linkage and conformational analysis. Structural refinement was carried out with the Amber and Glycam force fields (Hornak et al., *Proteins*, 2006, 65: 712-725; Kirschner et al., J Comput Chem. 2008, 29: 622-655). N-glycosylation scores were computed via the online server NetNGlyc 1.0 (DTU Health Tech; Gupta and Brunak, Pacific Symposium on Biocomputing, 2002, 7:310-322).

The sites designed according to the selection criteria listed above are highlighted in the sequence alignment (FIG. 6A) between the wild-type CH1 domain of the human IgG1 (SEQ ID NO:1), its single-point mutants introducing glycosylation sites at three positions, i.e., K129N, A158N and T191N (SEQ ID NO:2-4), and double (SEQ ID NO:5-7) and triple (SEQ ID NO:8) combinations thereof. Selected sites for de novo glycosylation appear to be well-conserved among the CH1 domains of other human IgG isoforms (SEQ ID NO: 9-11) according to a sequence alignment (FIG. 6B).

Figure 7:
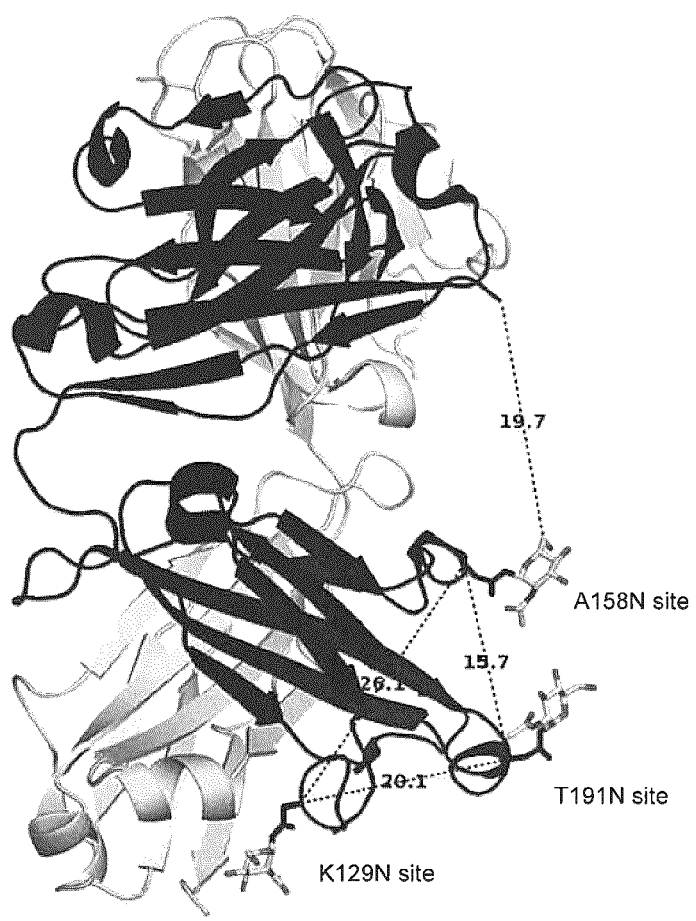
FIG. 7 illustrates the location of the de novo glycosylation sites highlighted on a typical Fab crystal structure of high resolution (PDB code 3MXW at 1.8 Å resolution, heavy chain in black, light chain in white rendering).

FIG. 7 shows the location of the de novo glycosylation sites highlighted on a typical Fab crystal structure of high resolution (PDB code 3MXW at 1.8 Å resolution, heavy chain in black, light chain in white rendering). Geometric measurements indicated that the distances between the alpha carbon atoms of the residues mutated to asparagine residues are larger than 15 Å, and each site is over 20 Å from at least another site. This is important in order to avoid overcrowding of glycan residues and excessive hydrophobicity upon drug linkage to multiple de novo sites simultaneously. The distance between modeled N-linked monosaccharides GlcNAc at the de novo sites and the variable domain is at least 15 Å. This advantageously ensures a minimal impact of the carbohydrate-linked drug on the variable domain bearing the antigen binding affinity determinants.

Figure 8:
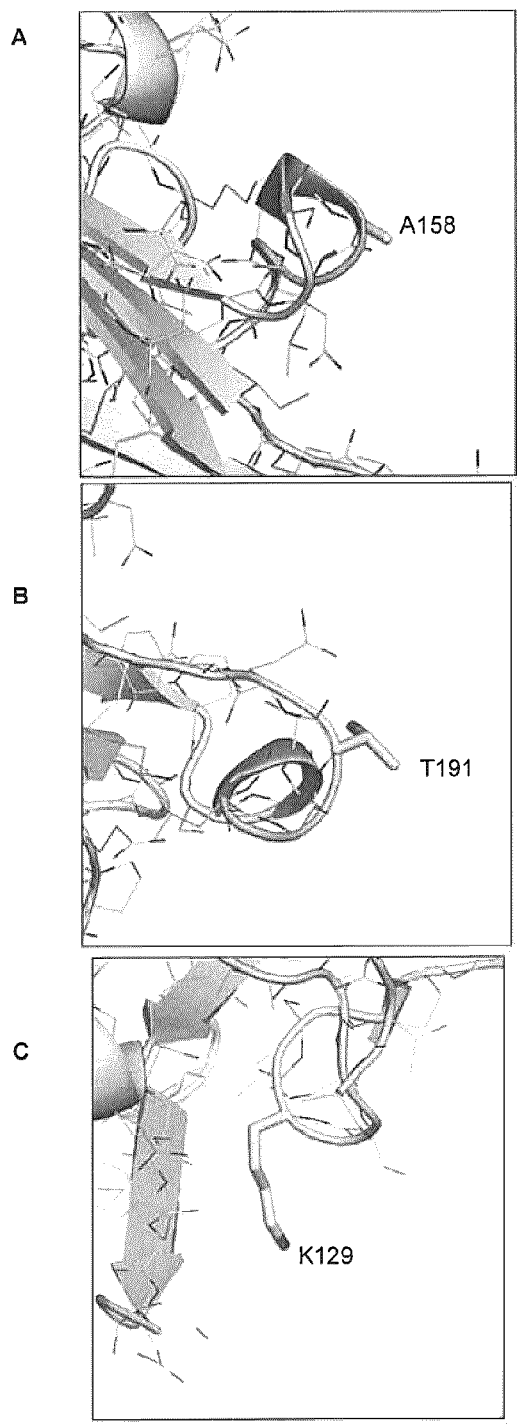
FIG. 8 illustrates the atomic environments around each wild-type mutated residue.

The wild-type residues mutated to the asparagines of the de novo sites are weakly involved in intramolecular interactions within the Fab. This is suggestive of small structural and stability changes upon introduction of these de novo glycosylation sites. The atomic environments around each wild-type mutated residue are shown in FIG. 8.

For comparison, the L189N mutant previously reported in U.S. Pat. No. 6,254,868 was included in this study.

Removal of Sialic Acid from Trastuzumab Wt and Mutants and Addition of Galactose Sialic acid was removed by treating the trastuzumab variants (final concentration 1.3 mg/mL) with a recombinant sialidase (loading of 0.05 unit per mg of trastuzumab) from *M. viridifaciens* (construct MNV-02) for 2 h at 37° C. in 50 mM Hepes pH 7. Galactose was added directly following the sialidase treatment using a recombinant version of the human beta-1,4-galactosyltransferase 1 expressed in *E. coli*. The reaction was performed with 1 mg/mL of trastuzumab, beta-1,4-galactosyltransferase 1 (loading of 0.04 unit per mg of trastuzumab), 10 mM $MnCl_2$, 10 mM UDP-Gal and 50 mM Hepes pH 7. The reaction was performed at 37° C. for 18 h. The trastuzumab variants were purified by applying the reaction mix to a 1 mL Protein A column equilibrated with PBS buffer pH 7.5. The trastuzumab variants were eluted with 100 mM citrate buffer pH 3 and the buffer was replaced with PBS pH 7.5 by desalting on a 5 mL HiTrap desalting column (GE Healthcare Life Sciences). In some cases, the purified material was purified a second time on Protein A to remove residual sialidase activity. The purified desialylated and galactosylated trastuzumab variants were concentrated to between 1.5 and 2 mg/mL using an Amicon Ultra-4 centrifugal filter unit with a 10,000 NMWL.

Addition of Neu5NAz to the Fc Glycans of Trastuzumab Wt

Neu5NAz was added to the Fc glycans of trastuzumab wt using ST6Gal1. The reaction mix included 1.22 mg/mL de-sialylated and galactosylated trastuzumab wt (total of 5.5 mg), 50 mM Hepes pH 7.5, 10 mM $MnCl_2$, 1 mM CMP-Neu5NAz and 137 mU of ST6Gal1. The reaction was performed at 37° C. for 24 h. The trastuzumab wt(Fc-Neu5NAz) was purified by applying the reaction mix to a 1 mL Protein A column equilibrated with PBS buffer pH 7.5. The TZMwt(Fc-Neu5NAz) was eluted with 100 mM citrate buffer pH 3 and the buffer was replaced with PBS pH 7.5 by desalting on a 5 mL HiTrap desalting column (GE Healthcare Life Sciences). The material was concentrated to 2.94 mg/mL (total of 4.33 mg recovered) using an Amicon Ultra-4 centrifugal filter unit with a 10,000 NMWL.

Addition of Neu5NAz to the Fd Glycans of Trastuzumab Mutants

Neu5NAz was added to the Fd glycans of trastuzumab mutants using the AST-03 alpha-2,3-sialyltransferase. The reaction mixes included 0.83 to 1.17 mg/mL de-sialylated and galactosylated trastuzumab mutants (total of 2.75 to 6.46 mg depending on the mutant), 50 mM Hepes pH 7, 10 mM $MnCl_2$, 1 mM CMP-Neu5NAz and 10 mU of AST-03 per mg of trastuzumab mutant. The reaction was performed at 37° C. for 18 h. The trastuzumab mutants (Fd-Neu5NAz) were purified by applying the reaction mixes to a 1 mL Protein A column equilibrated with PBS buffer pH 7.5. The trastuzumab mutants (Fd-Neu5NAz) were eluted with 100 mM citrate buffer pH 3 and the buffer was replaced with PBS pH 7.5 by desalting on a 5 mL HiTrap desalting column (GE Healthcare Life Sciences). The material was concentrated to 2.8 to 3.7 mg/mL (total of 2.7 to 5.3 mg recovered) using an Amicon Ultra-4 centrifugal filter unit with a 10,000 NMWL.

Labeling of Glyco-Engineered Trastuzumab Wt and Mutants with MB488-DBCO

The glyco-engineered tratuzumab wt (Fc-Neu5NAz) and trastuzumab mutants (Fd-Neu5NAz), all at 1.45 mg/mL (1 mg total), were reacted with 0.2 mM MB488-DBCO (Click Chemistry Tools) in PBS pH 7.4 for 24 h at 25° C. in the dark. The unreacted MB488-DBCO was removed by loading the reactions on PD Miditrap G-25 columns (GE Healthcare Life Sciences) and eluting with PBS pH 7.5. The degree of labeling was calculated using a molar extinction coefficient of 75,000 $M^{-1}$ $cm^{-1}$ at 494 nm for MB488 and a correction factor of 0.26 at 280 nm. We used a molar extinction coefficient of 201,197 $M^{-1}$ $cm^{-1}$ at 280 nm for trastuzumab. Pooling the most concentrated fractions yielded 0.77 mg of trast Fc-MB488 with a degree of labeling (DOL) of 1.31 while the recovery for trastuzumab mutants labeled on Fd with MB488 was 0.7 to 0.8 mg with a degree of labeling of 1.2 to 1.3.

Click Reactions of Glyco-Engineered Trastuzumab Wt and Mutants with DBCO-PEG4-VC-PAB-MMAE In order to increase the amount of incorporated Neu5NAz, a second reaction with either ST6Gal1 or AST-03 was performed as described above. The purified trastuzumab wt (Fc-Neu5NAz) and trastuzumab mutants (Fd-Neu5NAz) were purified as described above. The glyco-engineered trastuzumab wt (Fc-Neu5NAz) and trastuzumab single site mutants (Fd-Neu5NAz) at 2 mg/mL (0.7 mg total), was reacted with 0.11 mM DBCO-PEG4-VC-PAB-MMAE (Levena Biopharam) in 10% dimethylacetamide, 100 mM potassium phosphate, 20 mM NaCl, 2 mM EDTA, pH 7.2 for 24 h at 25° C. in the dark. The unreacted DBCO-PEG4-VC-PAB-MMAE was removed by loading the reaction on a 2 mL Zeba Spin Desalting column (Pierce) and eluting with 20 mM succinate, 0.02% Tween 20, pH 5.5, 6% trehalose. The desalting step was repeated for a total of three times. The drug to antibody ratio was calculated using molar extinction coefficients of 33,095 $M^{-1}$ $cm^{-1}$ at 248 nm and 7,615 $M^{-1}$ $cm^{-1}$ at 280 nm for clicked DBCO-PEG4-VC-PAB-MMAE. We used molar extinction coefficients 81,973 $M^{-1}$ $cm^{-1}$ at 248 nm of 215,380 $M^{-1}$ $cm^{-1}$ at 280 nm for trastuzumab. The recoveries were in the range of 0.47 to 0.58 mg with DAR's ranging from 1.33 to 1.88.

Glycoprofile Analysis by LC-MS of
Glyco-Engineered Trastuzumab Wt and Mutants,
and of Conjugates Glycoprofile analysis by LC-MS was performed as described in Raymond et al. (*Mabs* 2015, 7: 571-583) as described above for the glycoprofile analysis of glyco-engineered cetuximab and conjugates.

Cell Culture

Binding and functional testing was performed on cultured cell that are known to express the HER2. SKOV3 (human ovarian adenocarcinoma) and SKBr3 (human breast carcinoma) cell lines were obtained from ATCC and cultured according to supplier's recommendations. JIMT-1 (human breast carcinoma) cell line were obtained from AddexBlo and cultured according to supplier's recommendations. Cells were passaged twice a week and used within 4-6 weeks for all cell lines.

Target Binding by Flow Cytometry

Fluorescently labeled antibodies were tested for binding to breast cancer JIMT-1 cells. Adherent cells were dissociated with non-enzymatic Sigma Cell Dissociation Solution (Cat. No. C5789). Cell suspensions were added to polypropylene, V-bottom 96-well plates and incubated for 2 h on ice with 488-labeled antibodies at concentrations ranging from 100 nM to 0.001 nM. After incubation and washes, cell viability was determined using Fixable viability dye 450 (20 min on ice). Stained cells were fixed in 1% formaldehyde at 4° C. and stored at 4° C. until acquisition which was performed next day. Data acquisition was performed in the LSR-Fortessa Flow cytometer (Beckton Dickinson) equipped with FACS Diva Software and HTS unit (automated sampling in 96-well plates). FACS data was exported into Excel data files and MFI (Median Fluorescence intensity) of the AF488-stained, alive (single cells) peak was taken for calculations. Background subtraction was calculated for all wells using the MFI values of the cells incubated in the absence of secondary antibody. Background subtracted data was analyzed in GraphPad 6.0 using the One-site specific binding with Hill slope non-linear regression curve fit model to determine apparent Bmax and Kd for each of the test articles.

Growth Inhibition Assay

Glycoconjugates and controls were tested for their effects on viability on. Cells were seeded at 200 cells/well 384-well plates (Corning® 384 well white fat bottom polystyrene TC-treated microplates, Cat. #3570). Cells were allowed to grow for five days in the presence of serial dilutions of the test articles or benchmark controls ranging from 100 nM to 0.0017 nM. After five days (37° C., 5% $CO_2$, humidified incubator), the number of viable cells in culture was determined using CellTiterGlo (Promega, Madison), based on quantitation of the ATP present in each well, which signals the presence of metabolically active cells.

Signal output is measured on a luminescence plate reader (EnVision, Perkin Elmer) set at an integration time of 0.1 sec. Integration time is adjusted to minimize signal saturation at high ATP concentration Data analysis: Each concentration point (S) is normalized to the negative control wells (NC) and expressed as % survival.

$$\% \text{ survival} = \frac{NC - S}{NC \times 100}$$

Dose-response curves of % survival vs. log concentration were fit using GraphPad Prism 6.0 with a four parameter logistic model to estimate $IC_{50}$ and maximum efficacy.

$$\text{Model } Y = \frac{\text{Bottom} + (\text{Top} - \text{Bottom})}{1 + 10^{(\log IC50 - X) \times \text{HillSlope}}}$$

Where: $IC_{50}$ is the concentration of agonist that gives a response half way between Bottom and Top;

HillSlope describes the steepness of the curves.

Top and Bottom are plateaus in the units of the Y axis

If the curve was not complete, approximate $IC_{50}$ values (marked as ~) were estimated based on the mid point of the activity curve.

Results

De Novo N-Glycosylations Sites in Fd Region of
Trastuzumab Wt

Single De Novo Sites:

Three N-linked glycosylation sites were engineered (individually) in the Fd of trastuzumab. The constructs were expressed in CHO cells. Mass spectrometry analysis showed full occupancy of with N-linked glycans for the three new Fd sites (data not shown).

Figure 9:
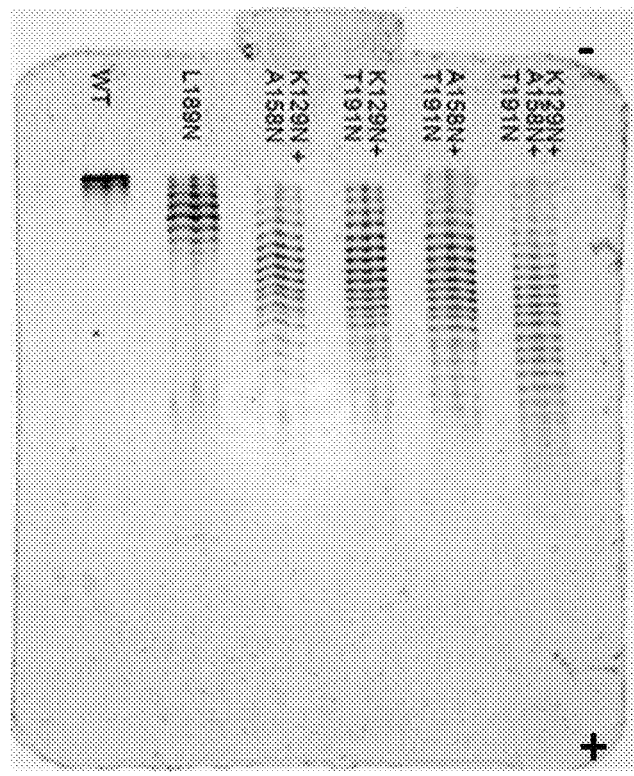
FIG. 9 illustrates isoelectricfocusing gel analysis (pH 3-9) of WT and mutant trastuzumab.

Combination De Novo Sites:

The 3 single N-linked mutants were combined in pairs and as a triple Fd mutant in trastuzumab. The double mutants and the triple mutant are shifted even more toward the positive electrode (anode) than a single mutant control (L189N shown in FIG. 9) on a isoelectrofocusing gel stained with Coomassie blue. This shift to more acidic forms confirms that the double and triple mutants have more sialylated N-glycans and consequently more sites for incorporation of azido-NeuAc, which could result in DAR increases.

Figure 10:
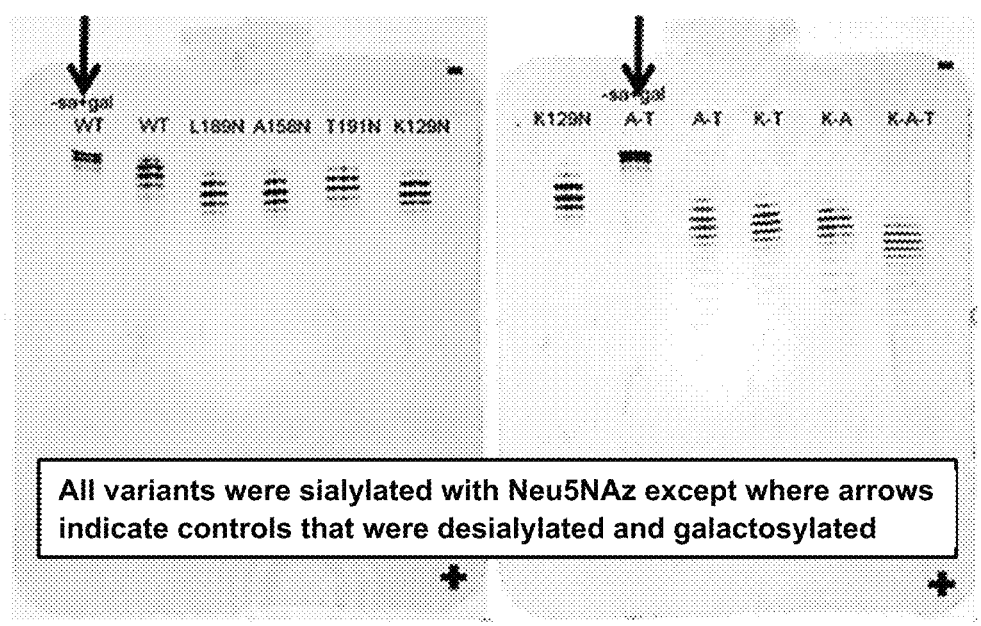
FIG. 10 illustrates isoelectricfocusing analysis (pH 3-9) of WT and mutant trastuzumab that were desialylated and galactosylated, and then treated with CMP-Neu5NAz with either ST6Gal1 (for trastuzumab WT) or AST-03 (for trastuzumab mutants). The double and triple mutants are designated by the amino acids that were mutated i.e. A-T corresponds to double mutant A158N and T191N, K-T corresponds to double mutant K129N and T191N, K-A corresponds to double mutant K129N and A158N and K-A-T corresponds to triple mutant K129N, A158N and T191N.

Addition of Neu5NAz to the Trastuzumab Mutants:

Modulation of the DARs could be obtained by removing the Neu5Ac with a sialidase and introducing Neu5NAz using AST-03. FIG. 10 shows shift toward the anode when there are additional introduced N-linked sites and following incubation of desialylated and galactosylated trastuzumab mutants with AST-03 and CMP-Neu5NAz. The distributions of isoelectric forms are also more uniform than the material before glyco-engineering (compare FIG. 9 versus FIG. 10), suggesting that modulation of DARs could be uniform.

Target Binding by Flow Cytometry

Figure 11:
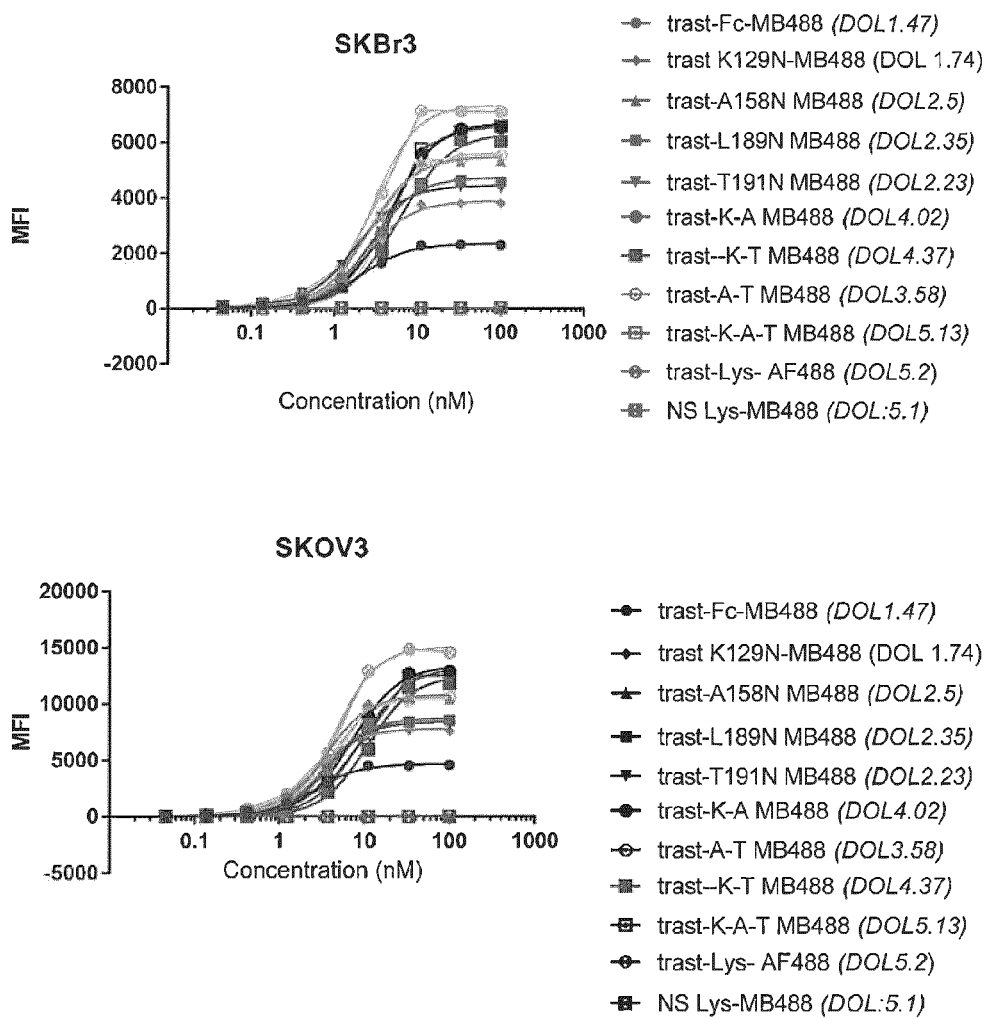
FIG. 11 demonstrates binding of glyco-engineered trastuzumab antibodies labeled with MB488 to HER2 expressing SKBr3 and SKOV3 cells.
Figure 12:
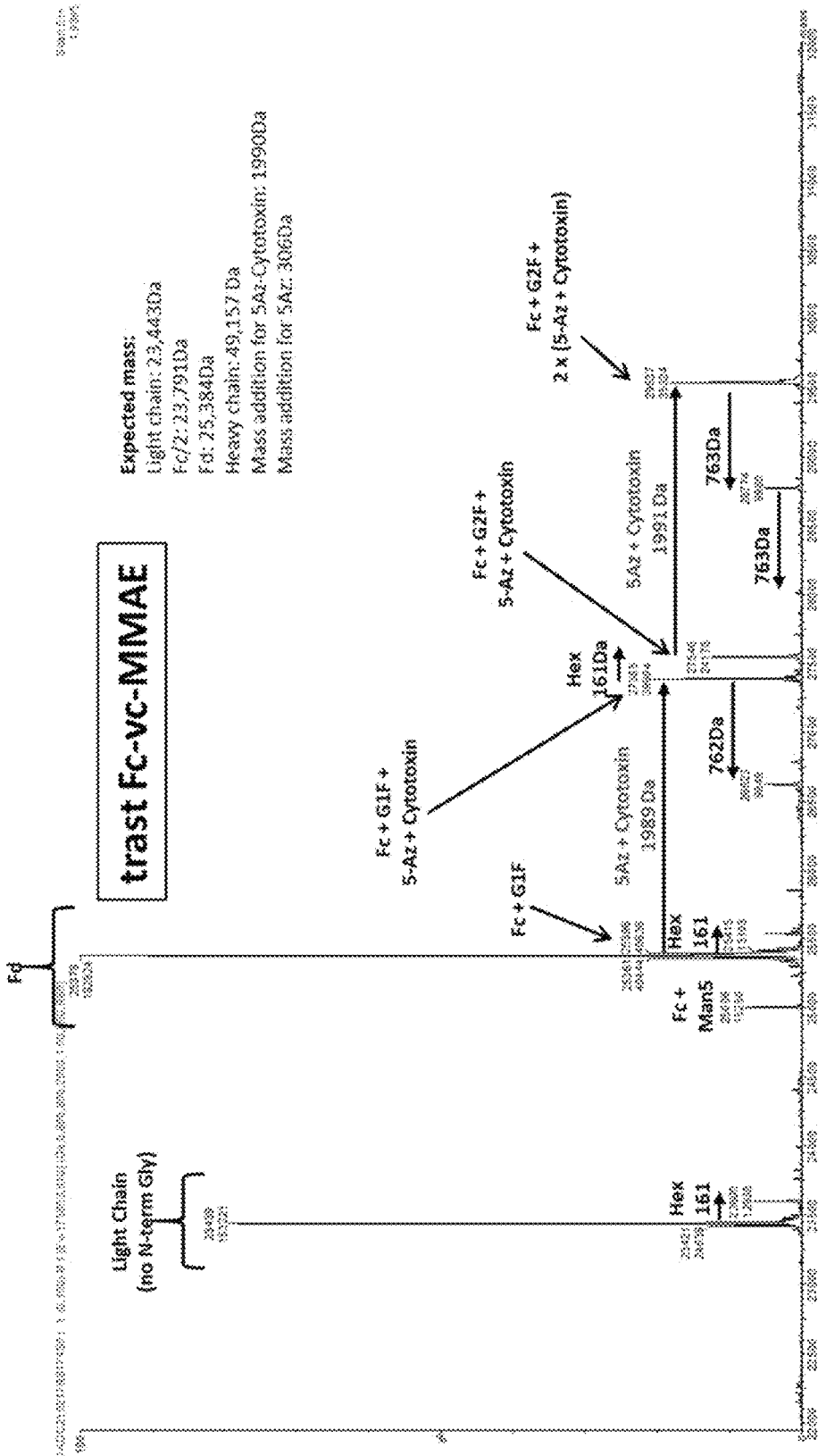
FIG. 12 illustrates mass spectrometry analysis of trast Fc-vc-MMAE (deconvoluted spectra).
Figure 13:
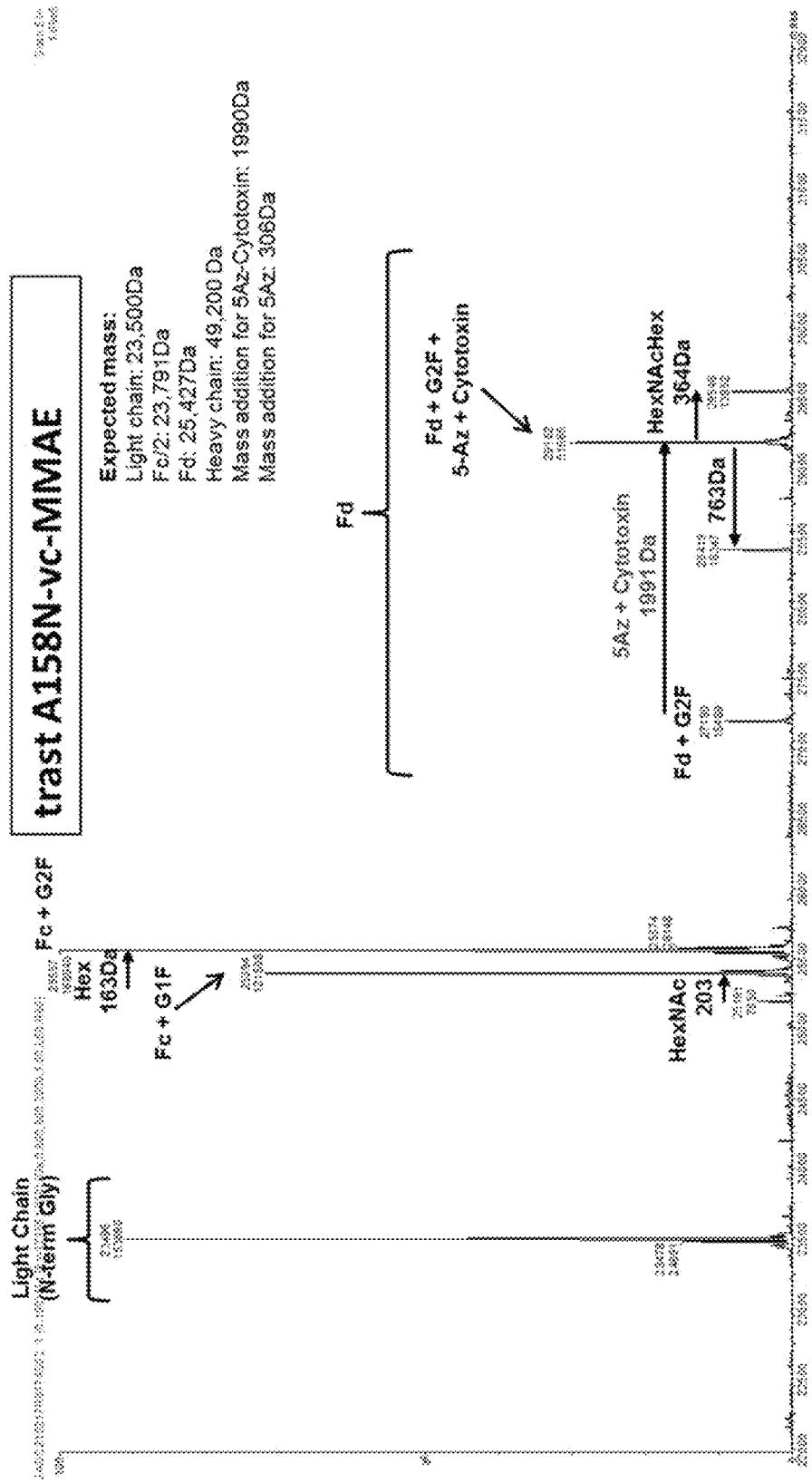
FIG. 13 illustrates mass spectrometry analysis of trast A158N-vc-MMAE (deconvoluted spectra).
Figure 14:
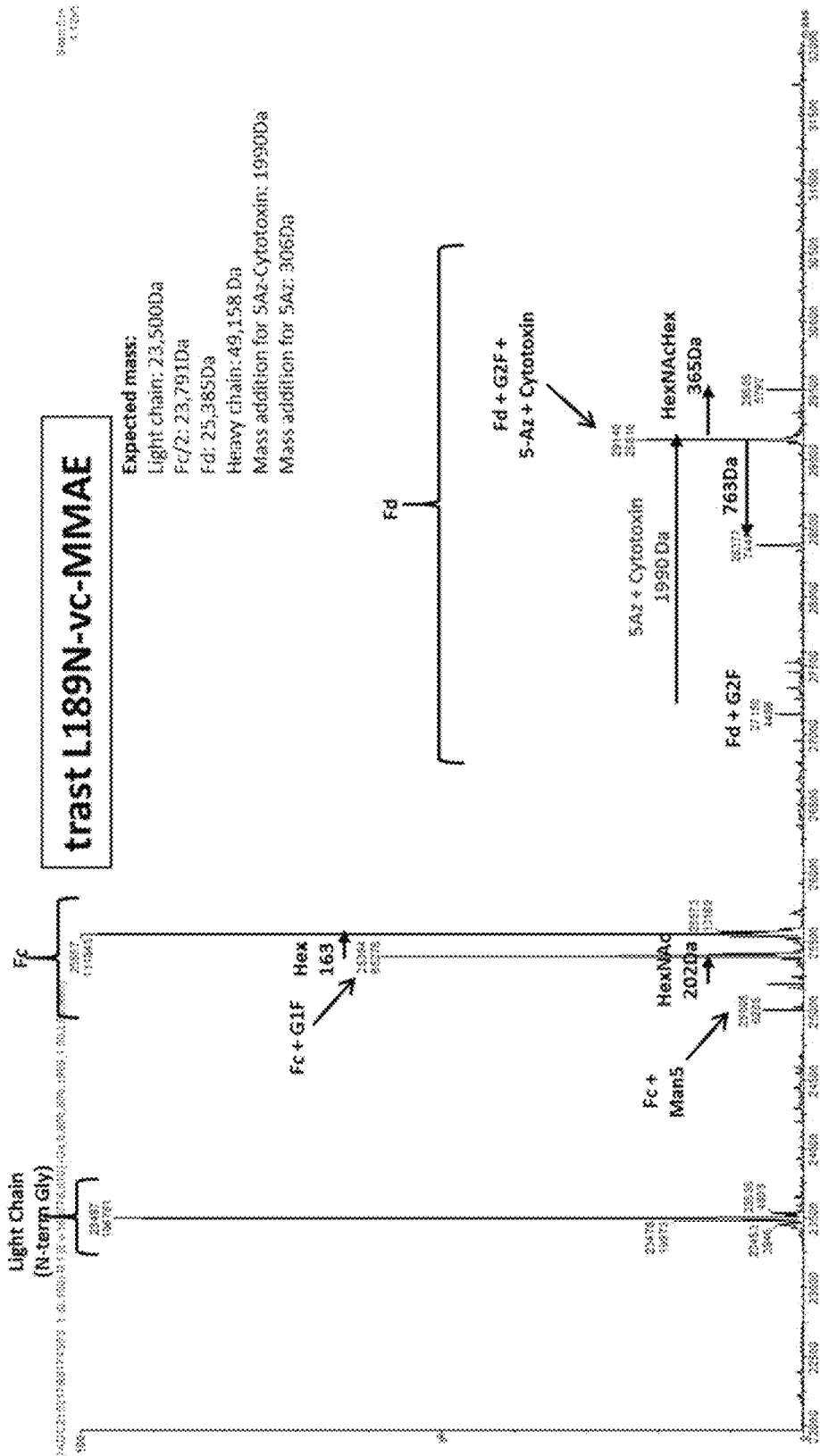
FIG. 14 illustrates mass spectrometry analysis of trast L189N-vc-MMAE (deconvoluted spectra).
Figure 15:
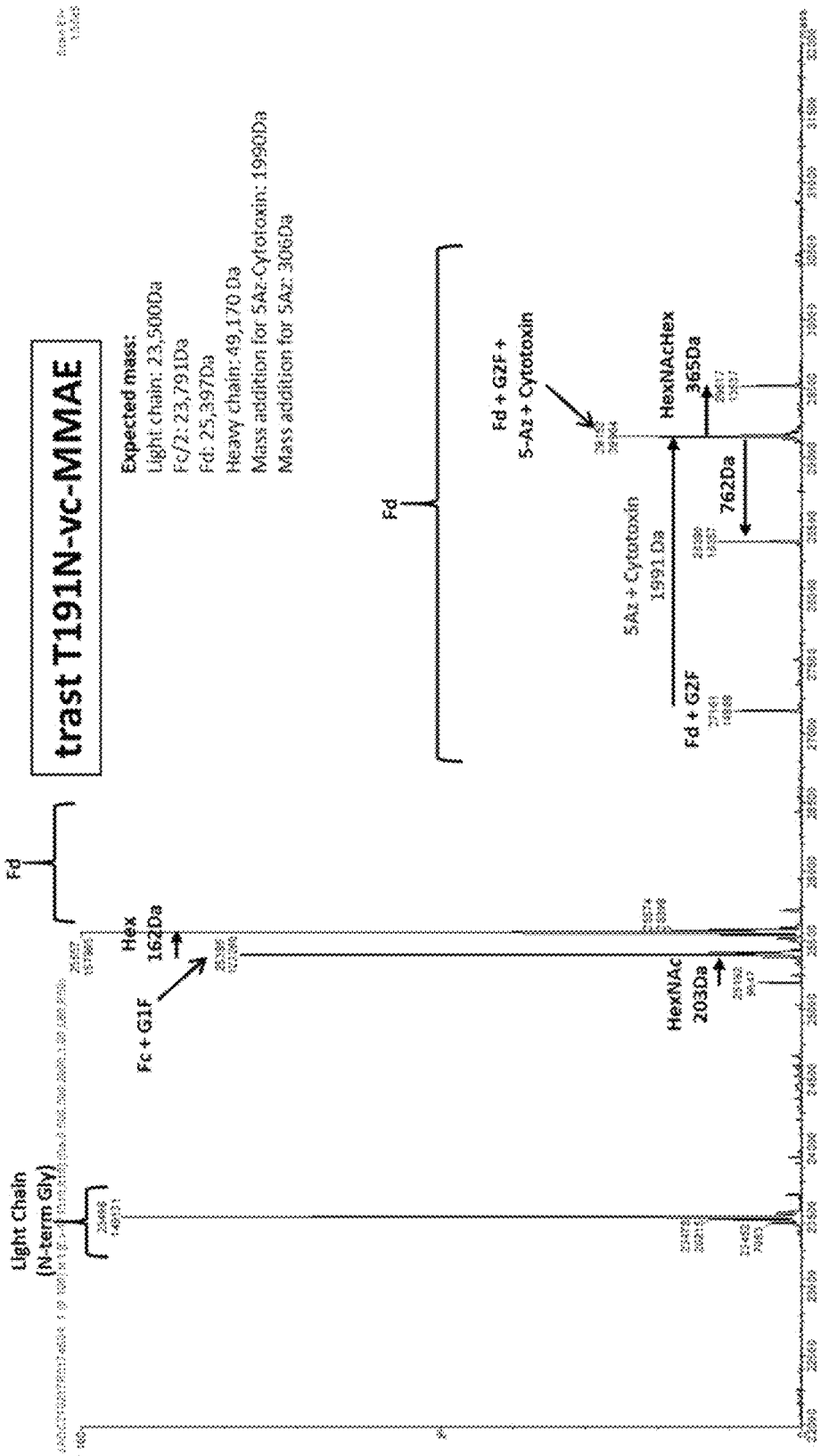
FIG. 15 illustrates mass spectrometry analysis of trast T191N-vc-MMAE (deconvoluted spectra).

Labeling of glyco-engineered trastuzumab mutants with MB488-DBCO resulted in a stoichiometry or degree of labelling (DOL) that correlated directly with the number of de novo glycosylation sites present in the antibodies for the single (DOL from 2.2-2.5) and double-conjugation site variants (DOL from 3.6-4.4) as indicated in the legend of FIG. 11. The antibody with 3 de novo glycosylation sites had a degree of labelling that was similar to that obtained with labelling of random Lys (DOL 5.1 vs 5.2). Notably, the wt antibody modified on the naturally occurring Fc glycosylation site using ST6-Gal1 (trast-Fc-MB488) had a DOL of 1.5, which is lower than any of the corresponding Fd conjugates modified on de novo Fd sites with AST-03. Cell surface binding of glyconjugated trastuzumab antibodies were tested on Her2 expressing SKBr3 and SKOV3 cells by flow cytometery (FIG. 11). In particular, antibodies containing de novo glycosylation sites were compared to those labeled on the Fc site (Asn297) as well as those labelled on random Lysine residues (Lys). As a negative control, binding of an irrelevant antibody (NS antibody Lys) was tested to determine levels of non-specific binding. Generally, the levels of mean fluorescence intensity at antibody saturation (Bmax) correlated well with the degree of labelling (DOL), suggesting that the sites of conjugation did not significantly affect antigen binding. On all cell lines tested, cell surface binding affinities (apparent Kd) were comparable amongst all the single site conjugates tested (ranging from 1.8-2.8 for SKBr3 and 2.5-3.7 for SKOV3, see Table 5) and higher in affinity to that of Lys conjugated trastuzumab. Similar results were observed using HER2 expressing breast cancer JIMT-1cells (profiles not shown). Affinity of the double and triple mutants was weaker than that of the corresponding single mutants with the exception of the K129N/A158N double mutant, whose apparent Kd was in the range obtained with the single mutants. The observed results confirm that the selected individual de novo glycosylation sites are an advantageously useful way of generating site-specific conjugation sites following modification by AST-03. Moreover, our results indicate that these sites can be combined together to generate higher stoichiometry labelling as needed.

TABLE 5

Apparent Kd determinations of glyco-engineered trastuzumab variants labelled with MB488 in Her2 expressing cell lines.

| | apparent Kd (nM) | | | |
|---|---|---|---|---|
| | SKOV3 | JIMT | SKOV3 (n = 2) | SKBr3 |
| NS Lys-MB488 | nb | NT | nb | nb |
| trast Lys-MB488 | 5.0 | ~5 | 4.6 | 2.9 |
| trast Fc-MB488 | 3.3 | NT | 2.5 | 2.0 |
| trast L189N-MB488 | 3.4 | NT | 3.5 | 2.7 |
| trast A158N-MB488 | 3.3 | 3.9 | 3.5 | 2.6 |
| trast K129N-MB488 | 3.1 | 3.2 | 2.5 | 2.3 |
| trast T191N-MB488 | NT | NT | 3.7 | 1.8 |
| trast-K-A MB488 | NT | NT | 7.1 | 4.5 |

TABLE 5-continued

Apparent Kd determinations of glyco-engineered trastuzumab variants labelled with MB488 in Her2 expressing cell lines.

| | apparent Kd (nM) | | | |
|---|---|---|---|---|
| | SKOV3 | JIMT | SKOV3 (n = 2) | SKBr3 |
| trast-K-T MB488 | NT | NT | 10.8 | 5.9 |
| trast-A-T MB488 | NT | NT | 4.0 | 2.6 |
| trast-K-A-T MB488 | NT | NT | 8.9 | 4.5 |

Glycoprofile Analysis by LC-MS of Glyco-Engineered Tratuzumab Wt and Tratuzumab Mutants Conjugated with MMAE Mass spectrometry analysis was used to determine the glycoprofile of tratuzumab wt labeled with Neu5NAz using ST6Gal1 and trastuzumab mutants labeled with Neu5NAz using AST-03 after conjugation with MMAE (FIGS. 12, 13, 14 and 15). The quantification of species is detailed in Tables 6 and 7 below. As expected because of the absence of any Fd glycan, trast Fc-vc-MMAE is modified with the drug only on the Fc glycan. The trastuzumab mutants were treated with AST-03 which resulted in very specific labeling of the Fd glycans for all of them.

TABLE 6

Glycoprofile of Fc of glyco-engineered trastuzumab variants after clicking with MMAE:

| Glycoform | trast-WT | trast-A158N | trast-L189N | trast-T191N |
|---|---|---|---|---|
| Man5 | 8 | 0 | 3 | 0 |
| Man6 | 0 | 0 | 1 | 0 |
| HexNAc$_3$Hex$_4$Fuc | 0 | 3 | 3 | 3 |
| G0F | 2 | 1 | 0 | 0 |
| G1F | 22 | 40 | 34 | 42 |
| HexNAc$_5$Hex$_3$Fuc | 4 | 0 | 0 | 0 |
| G2F | 2 | 56 | 58 | 54 |
| G1F + 5-Az + MMAE | 21 | 0 | 0 | 0 |
| G2F + 5-Az + MMAE | 13 | 0 | 0 | 0 |
| G2F + 2(5-Az + MMAE) | 19 | 0 | 0 | 0 |
| G1F + 5-Az + MMAE − 762Da | 5 | 0 | 0 | 0 |
| G2F + 2(5-Az + MMAE) − 762Da | 5 | 0 | 0 | 0 |

TABLE 7

Glycoprofile of Fd of glyco-engineered trastuzumab variants after clicking with MMAE.

| Glycoform | trast-WT | trast-A158N | trast-L189N | trast-T191N |
|---|---|---|---|---|
| None | 100 | 0 | 0 | 0 |
| G1F | 0 | 0 | 0 | 0 |
| G2F | 0 | 16 | 10 | 17 |
| G3F | 0 | 1 | 0 | 0 |
| G2F + 5-Az + MMAE | 0 | 52 | 59 | 45 |
| G2F + 5-Az + MMAE − 762Da | 0 | 17 | 17 | 21 |
| G3F + 5Az + MMAE | 0 | 14 | 13 | 15 |
| G2F + 2(5-Az + MMAE) | 0 | 0 | 0 | 1 |

Figure 16:
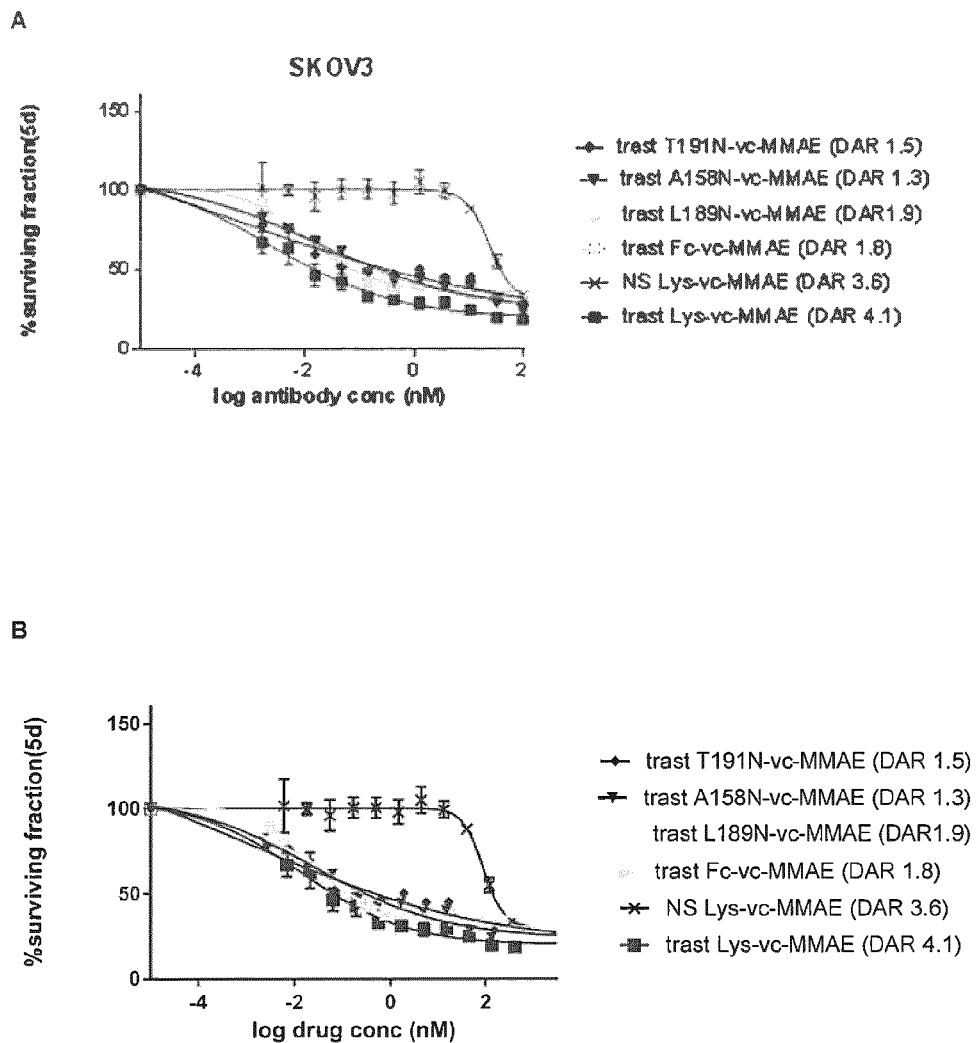
FIG. 16 demonstrates growth inhibitory effect of glyco-engineered trastuzumab wt and mutants conjugated with DBCO-vc-PAB-MMAE in Her2 expressing cells. Potency was determined according to concentration of antibody (Panel A) or MMAE (Panel B).

Growth inhibition activity of glyconjugated trastuzumab antibodies were compared to those labeled on random Lysine residues (Lys) on Her2 expressing SKOV3 cells as described above. As a negative control, activity of an irrelevant antibody (NS antibody Cys) was tested to determine levels of non-specific growth inhibition activity. All conjugated trastuzumab antibodies were shown to be active in causing growth inhibition in Her2 overexpressing SKOV3 ovarian cancer cells relative to the non-targeted ADC, NS Lys-vc-MMAE. In particular, trastuzumab variants that were conjugated to indicated de novo glycosylation sites in the CH1 domain of mAbs were comparable in their ability to cause growth inhibition as compared to antibodies glycosylated and conjugated in the Fc domain (FIG. 16A). This was also shown to be the case when ADC potency was calculated on the concentration of the drug added (FIG. 16B).

TABLE 8

IC$_{50}$ determinations of MMAE-glyco-engineered tratuzumab in Her2 overexpressing SKOV3 ovarian cancer cells.

| | ADC IC$_{50}$ (nM) | MMAE IC$_{50}$ (nM) |
|---|---|---|
| trast Fc-vc-MMAE | 0.01 | 0.02 |
| trast A158N-vc-MMAE | 0.01 | 0.02 |
| trast L189N-vc-MMAE | 0.01 | 0.02 |
| trast T191N-vc-MMAE | 0.01 | 0.02 |
| trast Lys-vc-MMAE | 0.002 | 0.01 |
| NS Lys-vc-MMAE | 24.6 | 87.9 |

Sequences

SEQ ID NO: 1 hIgG1CH1
ASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKV

SEQ ID NO: 2 hIgG1CH1-K129N
ASTKGPSVFPLAPSSNSTSGGTAALGCLVKDYFPEPVTVSWNSGALTSGVHTFPAVLQSS
GLYSLSSVVTVPSSSLGTQTYICNVNHKPSNTKVDKKV

SEQ ID NO: 3 hIgG1CH1-A158N
ASTKGPSVFPLAPSSKSTSGGTAALGCLVKDYFPEPVTVSWNSGNLTSGVHTFPAVLQSS
GLYSLSSVVTVPSSSLGTQTYICNVNHKPSNTKVDKKV

SEQ ID NO: 4 hIgG1CH1-T191N
ASTKGPSVFPLAPSSKSTSGGTAALGCLVKDYFPEPVTVSWNSGALTSGVHTFPAVLQSSG
LYSLSSVVTVPSSSLGNQTYICNVNHKPSNTKVDKKV

SEQ ID NO: 5 hIgG1CH1-K129N + A158N
ASTKGPSVFPLAPSSNSTSGGTAALGCLVKDYFPEPVTVSWNSGNLTSGVHTFPAVLQSS
GLYSLSSVVTVPSSSLGTQTYICNVNHKPSNTKVDKKV

SEQ ID NO: 6 hIgG1CH1-K129N + T191N
ASTKGPSVFPLAPSSNSTSGGTAALGCLVKDYFPEPVTVSWNSGALTSGVHTFPAVLQSS
GLYSLSSVVTVPSSSLGNQTYICNVNHKPSNTKVDKKV

SEQ ID NO: 7 hIgG1CH1-A158N + T191N
ASTKGPSVFPLAPSSKSTSGGTAALGCLVKDYFPEPVTVSWNSGNLTSGVHTFPAVLQSS
GLYSLSSVVTVPSSSLGNQTYICNVNHKPSNTKVDKKV

SEQ ID NO: 8 hIgG1CH1-K129N + A158N + T191N
ASTKGPSVFPLAPSSNSTSGGTAALGCLVKDYFPEPVTVSWNSGNLTSGVHTFPAVLQSS
GLYSLSSVVTVPSSSLGNQTYICNVNHKPSNTKVDKKV

SEQ ID NO: 9 hIgG2CH1
ASTKGPSVFPLAPCSRSTSESTAALGCLVKDYFPEPVTVSWNSGALTSGVHTFPAVLQSSG
LYSLSSVVTVPSSNFGTQTYTCNVDHKPSNTKVDKTV

SEQ ID NO: 10 hIgG3CH1
ASTKGPSVFPLAPCSRSTSGGTAALGCLVKDYFPEPVTVSWNSGALTSGVHTFPAVLQSS
GLYSLSSVVTVPSSSLGTQTYTCNVNHKPSNTKVDKRV

SEQ ID NO: 11 hIgG4CH1
ASTKGPSVFPLAPCSRSTSESTAALGCLVKDYFPEPVTVSWNSGALTSGVHTFPAVLQSSG
LYSLSSVVTVPSSSLGTKTYTCNVDHKPSNTKVDKRV

SEQ ID NO: 12 GenBank Accession #AFU19871
MERTPQLQAVDIYIDFATIPSLSYFLHFLKHKHDDQRLRLFSLARFEMPQTLIEQYEGI
IQFSRNVEHNVEPLLEQLQTILSQEGKQFELHLHLNLFHSFEMFLNLSPTYTQYKEKI
SKIVLHLYDDGSEVMKQYQLQKSSSLVQDLAATKASLVSLFENGEGSFSQIDLIRY
VWNAVLETHYYLLSDHFLLDEKLQPLKAELGHYQLLNLSAYQYLSSEDLLWLKQILKI
DTELESLMQKLTAQPVYFFSGTTFFNISFEDKQRLANIHAILIREHLDPNSQLFIGEPY
LFVFKGHPNSPEINQALREYYPNVIFLPENIPFEILTLLGFSPQKIGGFASTIHVNSEQ
SKLAKLFFLTSTDEQERQLSDGYIKQYALAQAMLEMQLVSQEQVYYCSLSS SEQ ID NO: 13 primer AS-01
5' CGTAGCGATACATATGGAAAGAACCCCCCAACTAC 3'

SEQ ID NO: 14 primer AS-02
5' CTGAAGGTCGACATTATGAGGACAAACTACAATAATAC 3'

REFERENCES

All patents, patent applications and publications referred to herein and throughout the application are hereby incorporated by reference.

Arnold J N, Wormald M R, Sim R B, Rudd P M, Dwek R A. (2007) The impact of glycosylation on the biological function and structure of human immunoglobulins. *Annu. Rev. Immunol.* 25:21-50.

Axup J Y, Bajjuri K M, Ritland M, Hutchins B M, Kim C H, Kazane S A, Halder R, Forsyth J S, Santidrian A F, Staflin K, Lu Y, Tran H, Seller A J, Biroc S L, Szydlik A, Pinkstaff J K, Tian F, Sinha S C, Felding-Habermann B, Smider V V, Schultz P G. (2012) Synthesis of site-specific antibody-drug conjugates using unnatural amino acids. *Proc. Natl. Acad. Sci. USA.* 109:16101-16106.

Boons, G.-J. Site-specific antibody-drug glycoconjugates and methods. WO2015/157446.

Ducry L, Stump B. (2010) Antibody-drug conjugates: linking cytotoxic payloads to monoclonal antibodies. *Bioconjug. Chem.* 21:5-13.

Gupta R, Brunak S. (2002) Prediction of glycosylation across the human proteome and the correlation to protein function. *Pac. Symp. Biocomput.* 7:310-22

Hornak V, Abel R, Okur A, Strockbine B, Roitberg A, Simmerling C. (2006) Comparison of multiple Amber force fields and development of improved protein backbone parameters. *Proteins* 65:712-725.

Huang H S, Nagane M, Klingbeil C K, Lin H, Nishikawa R, Ji X D, Huang C M, Gill G N, Wiley H S, Cavenee W K. (1997) The enhanced tumorigenic activity of a mutant epidermal growth factor receptor common in human cancers is mediated by threshold levels of constitutive tyrosine phosphorylation and unattenuated signaling. *J. Biol. Chem.* 272:2927-2935.

Hutchins B M, Kazane S A, Staflin K, Forsyth J S, Felding-Habermann B, Schultz P G, Smider V V. (2011) Site-specific coupling and sterically controlled formation of multimeric antibody fab fragments with unnatural amino acids. *J. Mol. Biol.* 406:595-603.

Jefferis R. (2005) Glycosylation of recombinant antibody therapeutics. *Biotechnol. Prog.* 21:11-16.

Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Site-specific conjugation of a cytotoxic drug to an antibody improves the therapeutic index. *Nat. Biotechnol.* 26:925-932.

Kirschner K N, Yongye A B, Tschampel S M, Gonzalez-Outeirino J, Daniels C R, Foley B L, Woods R J. (2008) GLYCAM06: a generalizable biomolecular force field. Carbohydrates. *J. Comput. Chem.* 29:622-655.

Li X, Fang T, Boons G J. (2014) Preparation of well-defined antibody-drug conjugates through glycan remodeling and strain-promoted azide-alkyne cycloadditions. *Angew. Chem. Int. Ed. Engl.* 53:7179-7182.

Panowski S, Bhakta S, Raab H, Polakis P, Junutula J R. (2014) Site-specific antibody drug conjugates for cancer therapy. *MAbs.* 6:34-45.

Qian J, Liu T, Yang L, Daus A, Crowley R, Zhou Q. (2007) Structural characterization of N-linked oligosaccharides on monoclonal antibody cetuximab by the combination of orthogonal matrix-assisted laser desorption/ionization hybrid quadrupole-quadrupole time-of-flight tandem mass spectrometry and sequential enzymatic digestion. *Anal. Biochem.* 364:8-18.

Raymond C, Robotham A, Spearman M, Butler M, Kelly J, Durocher Y. (2015) Production of α2,6-sialylated IgG1 in CHO cells. *MAbs.* 7:571-583.

Strop P, Liu S H, Dorywalska M, Delaria K, Dushin R G, Tran T T, Ho W H, Farias S, Casas M G, Abdiche Y, Zhou D, Chandrasekaran R, Samain C, Loo C, Rossi A, Rickert M, Krimm S, Wong T, Chin S M, Yu J, Dilley J, Chaparro-Riggers J, Filzen G F, O'Donnell C J, Wang F, Myers J S, Pons J, Shelton D L, Rajpal A. (2013) Location matters: site of conjugation modulates stability and pharmacokinetics of antibody drug conjugates. *Chem. Biol.* 20:161-167.

van Dellft, F. L., van Geel, R., Wijdeven, M. A. (2016) Glycoengineered antibody, antibody-conjugate and methods for their preparation. US Patent Application 2016/0257764.

van Geel R, Wijdeven M A, Heesbeen R, Verkade J M, Wasiel A A, van Berkel S S, van Delft F L. (2015) Chemoenzymatic conjugation of toxic payloads to the globally conserved N-glycan of native mAbs provides homogeneous and highly efficacious antibody-drug conjugates. *Bioconjug. Chem.* 26:2233-2242.

Wakarchuk W W, Cunningham A M. (2003) Capillary electrophoresis as an assay method for monitoring glycosyltransferase activity. *Methods Mol. Biol.* 213:263-274.

Watson D C, Wakarchuk W W, Gervais C, Durocher Y, Robotham A, Fernandes S M, Schnaar R L, Young N M, Gilbert M. (2015) Preparation of legionaminic acid analogs of sialo-glycoconjugates by means of mammalian sialyltransferases. *Glycoconj. J.* 32:729-734

---

The invention claimed is:

1. An antibody comprising at least one N-linked glycan having a functionalized sialic acid in an Fab region of the antibody and at least one N-linked glycan without functionalized sialic acid in an Fc region of the antibody, wherein the at least one N-linked glycan having a functionalized sialic acid in an Fab region of the antibody is located at amino acid position 129, 158, and/or 191, and wherein the amino acid positions are numbered according to a wild type human IgG heavy chain sequence based on sequential numbering.

2. The antibody of claim 1, wherein the functionalized sialic acid is an azido-modified sialic acid.

3. The antibody of claim 1, wherein the antibody is an IgG, IgG1, IgA2, IgE, or IgM antibody.

4. The antibody of claim 2, wherein the functionalized sialic acid is N-azidoacetylneuraminic acid.

5. The antibody of claim 1, wherein the antibody is a modified cetuximab.

6. The antibody of claim 5, further comprising a cargo covalently attached to the functionalized sialic acid.

7. The antibody of claim 1, wherein the antibody is a modified trastuzumab, wherein the modification is in a CH1 domain.

8. The antibody of claim 7, wherein the modified trastuzumab comprises at least one mutation in the Fd region, wherein the at least one mutation is chosen from: K129N; A158N; T191N; K129N+A158N+T191N; A158N+T191N; K129N+T191N; and K129N+A158N, wherein the amino acids are numbered according to a wild type human IgG heavy chain sequence based on sequential numbering.

9. The antibody of claim 2, wherein the antibody is a modified trastuzumab, wherein the modification is in a CH1 domain.

10. The antibody of claim 7, further comprising a cargo covalently attached to the functionalized sialic acid.

11. A method of preparing the antibody of claim 1, the method comprising contacting an antibody comprising at least one N-linked glycan in an Fab region with a functionalized CMP-sialic acid and a bacterial sialyltransferase specific for the at least one N-linked glycan in the Fab region for a time and under conditions sufficient to covalently attach the functionalized sialic acid to the at least one N-linked glycan.

12. The method of claim 11, wherein the bacterial sialyltransferase is derived from *Actinobacillus suis*.

13. The method of claim 11, further comprising covalently linking a cargo to the functionalized sialic acid to yield an antibody conjugate.

14. The method of claim 11, wherein the antibody is cetuximab.

15. The method of claim 11, wherein the antibody is a genetically modified trastuzumab comprising at least one glycosylation site in an Fab domain.

16. An antibody glycoconjugate produced by contacting an antibody comprising at least one N-linked glycan in the antibody Fab region with a functionalized CMP-sialic acid and a bacterial sialyltransferase specific for N-linked glycan in the antibody Fab region for a time and under conditions sufficient to covalently attach the functionalized sialic acid to the at least one N-linked glycan in the antibody Fab region.

17. The method of claim 11, wherein the functionalized sialic acid is an azido-modified sialic acid, a functionalized N-acetylneuraminic acid, or an N-azidoacetylneuraminic acid.

18. The method of claim 13, wherein the step of covalently linking a cargo is carried out using click chemistry.

19. The method of claim 15, wherein the genetically modified trastuzumab comprises at least one mutation in an Fd region, wherein the at least one mutation is selected from: K129N; A158N; T191N; K129N+A158N+T191N; A158N+T191N; K129N+T191N; and K129N+A158N.

* * * * *

SEQUENCE LISTING

```
<160> NUMBER OF SEQ ID NOS: 15

<210> SEQ ID NO 1
<211> LENGTH: 98
<212> TYPE: PRT
<213> ORGANISM: Artificial Sequence
<220> FEATURE:
<223> OTHER INFORMATION: hIgG1CH1

<400> SEQUENCE: 1

Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 2
<211> LENGTH: 98
<212> TYPE: PRT
<213> ORGANISM: Artificial Sequence
<220> FEATURE:
<223> OTHER INFORMATION: hIgG1CH1-K129N

<400> SEQUENCE: 2

Ala Ser Thr Lys Gly Pro Ser Val Phe Pro Leu Ala Pro Ser Ser Asn
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 3
<211> LENGTH: 98
<212> TYPE: PRT
<213> ORGANISM: Artificial Sequence
<220> FEATURE:
<223> OTHER INFORMATION: hIgG1CH1-A158N

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Asn Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

```
<210> SEQ ID NO 4
<211> LENGTH: 98
<212> TYPE: PRT
<213> ORGANISM: Artificial Sequence
<220> FEATURE:
<223> OTHER INFORMATION: hIgG1CH1-T191N

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Asn Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 5
<211> LENGTH: 98
<212> TYPE: PRT
<213> ORGANISM: Artificial Sequence
<220> FEATURE:
<223> OTHER INFORMATION: hIgG1CH1-K129N+A158N

<400> SEQUENCE: 5

Ala Ser Thr Lys Gly Pro Ser Val Phe Pro Leu Ala Pro Ser Ser Asn
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Asn Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 6
<211> LENGTH: 98
<212> TYPE: PRT
<213> ORGANISM: Artificial Sequence
<220> FEATURE:
<223> OTHER INFORMATION: hIgG1CH1-K129N+T191N

<400> SEQUENCE: 6

Ala Ser Thr Lys Gly Pro Ser Val Phe Pro Leu Ala Pro Ser Ser Asn
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
Leu Ser Ser Val Val Thr Val Pro Ser Ser Leu Gly Asn Gln Thr
 65                  70                  75                  80

Tyr Ile Cys Asn Val Asn His Lys Pro Ser Asn Thr Lys Val Asp Lys
                 85                  90                  95

Lys Val

<210> SEQ ID NO 7
<211> LENGTH: 98
<212> TYPE: PRT
<213> ORGANISM: Artificial Sequence
<220> FEATURE:
<223> OTHER INFORMATION: hIgG1CH1-A158N+T191N

<400> SEQUENCE: 7

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Asn Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Asn Gln Thr
 65                  70                  75                  80

Tyr Ile Cys Asn Val Asn His Lys Pro Ser Asn Thr Lys Val Asp Lys
                 85                  90                  95

Lys Val

<210> SEQ ID NO 8
<211> LENGTH: 98
<212> TYPE: PRT
<213> ORGANISM: Artificial Sequence
<220> FEATURE:
<223> OTHER INFORMATION: hIgG1CH1-K129N+A158N+T191N

<400> SEQUENCE: 8

Ala Ser Thr Lys Gly Pro Ser Val Phe Pro Leu Ala Pro Ser Ser Asn
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Asn Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Asn Gln Thr
 65                  70                  75                  80

Tyr Ile Cys Asn Val Asn His Lys Pro Ser Asn Thr Lys Val Asp Lys
                 85                  90                  95

Lys Val

<210> SEQ ID NO 9
<211> LENGTH: 98
<212> TYPE: PRT
<213> ORGANISM: Artificial Sequence
<220> FEATURE:
<223> OTHER INFORMATION: hIgG2CH1

<400> SEQUENCE: 9
```

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 10
<211> LENGTH: 98
<212> TYPE: PRT
<213> ORGANISM: Artificial Sequence
<220> FEATURE:
<223> OTHER INFORMATION: hIgG3CH1

<400> SEQUENCE: 10

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 11
<211> LENGTH: 98
<212> TYPE: PRT
<213> ORGANISM: Artificial Sequence
<220> FEATURE:
<223> OTHER INFORMATION: hIgG4CH1

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 12
<211> LENGTH: 401
<212> TYPE: PRT
<213> ORGANISM: Actinobacillus suis

<400> SEQUENCE: 12

Met Glu Arg Thr Pro Gln Leu Gln Ala Val Asp Ile Tyr Ile Asp Phe
1               5                   10                  15

Ala Thr Ile Pro Ser Leu Ser Tyr Phe Leu His Phe Leu Lys His Lys
            20                  25                  30

His Asp Asp Gln Arg Leu Arg Leu Phe Ser Leu Ala Arg Phe Glu Met
        35                  40                  45

Pro Gln Thr Leu Ile Glu Gln Tyr Glu Gly Ile Ile Gln Phe Ser Arg
    50                  55                  60

Asn Val Glu His Asn Val Glu Pro Leu Leu Glu Gln Leu Gln Thr Ile
65                  70                  75                  80

Leu Ser Gln Glu Gly Lys Gln Phe Glu Leu His Leu His Leu Asn Leu
                85                  90                  95

Phe His Ser Phe Glu Met Phe Leu Asn Leu Ser Pro Thr Tyr Thr Gln
            100                 105                 110

Tyr Lys Glu Lys Ile Ser Lys Ile Val Leu His Leu Tyr Asp Asp Gly
        115                 120                 125

Ser Glu Gly Val Met Lys Gln Tyr Gln Leu Gln Lys Ser Ser Ser Leu
    130                 135                 140

Val Gln Asp Leu Ala Ala Thr Lys Ala Ser Leu Val Ser Leu Phe Glu
145                 150                 155                 160

Asn Gly Glu Gly Ser Phe Ser Gln Ile Asp Leu Ile Arg Tyr Val Trp
                165                 170                 175

Asn Ala Val Leu Glu Thr His Tyr Tyr Leu Leu Ser Asp His Phe Leu
            180                 185                 190

Leu Asp Glu Lys Leu Gln Pro Leu Lys Ala Glu Leu Gly His Tyr Gln
        195                 200                 205

Leu Leu Asn Leu Ser Ala Tyr Gln Tyr Leu Ser Ser Glu Asp Leu Leu
    210                 215                 220

Trp Leu Lys Gln Ile Leu Lys Ile Asp Thr Glu Leu Glu Ser Leu Met
225                 230                 235                 240

Gln Lys Leu Thr Ala Gln Pro Val Tyr Phe Phe Ser Gly Thr Thr Phe
                245                 250                 255

Phe Asn Ile Ser Phe Glu Asp Lys Gln Arg Leu Ala Asn Ile His Ala
            260                 265                 270

Ile Leu Ile Arg Glu His Leu Asp Pro Asn Ser Gln Leu Phe Ile Gly
        275                 280                 285

Glu Pro Tyr Leu Phe Val Phe Lys Gly His Pro Asn Ser Pro Glu Ile
    290                 295                 300

Asn Gln Ala Leu Arg Glu Tyr Tyr Pro Asn Val Ile Phe Leu Pro Glu
305                 310                 315                 320

Asn Ile Pro Phe Glu Ile Leu Thr Leu Leu Gly Phe Ser Pro Gln Lys
                325                 330                 335

Ile Gly Gly Phe Ala Ser Thr Ile His Val Asn Ser Glu Gln Ser Lys
            340                 345                 350

Leu Ala Lys Leu Phe Phe Leu Thr Ser Thr Asp Glu Gln Glu Arg Gln
        355                 360                 365

```
Leu Ser Asp Gly Tyr Ile Lys Gln Tyr Ala Leu Ala Gln Ala Met Leu
    370                 375                 380

Glu Met Gln Leu Val Ser Gln Glu Gln Val Tyr Tyr Cys Ser Leu Ser
385                 390                 395                 400

Ser

<210> SEQ ID NO 13
<211> LENGTH: 35
<212> TYPE: DNA
<213> ORGANISM: Artificial Sequence
<220> FEATURE:
<223> OTHER INFORMATION: primer AS-01

<400> SEQUENCE: 13
cgtagcgata catatggaaa gaaccccca actac                              35

<210> SEQ ID NO 14
<211> LENGTH: 38
<212> TYPE: DNA
<213> ORGANISM: Artificial Sequence
<220> FEATURE:
<223> OTHER INFORMATION: primer AS-02

<400> SEQUENCE: 14
ctgaaggtcg acattatgag gacaaactac aataatac                          38

<210> SEQ ID NO 15
<211> LENGTH: 12
<212> TYPE: PRT
<213> ORGANISM: Artificial Sequence
<220> FEATURE:
<223> OTHER INFORMATION: C-terminal tag

<400> SEQUENCE: 15

Gly His His His His His His His His His His Gly
1               5                   10
```